(12) United States Patent
Kim et al.

(10) Patent No.: US 11,331,350 B2
(45) Date of Patent: May 17, 2022

(54) **USE OF *MYCOBACTERIUM PARAGORDONAE* FOR CANCER IMMUNOTHERAPY**

(71) Applicant: SEOUL NATIONAL UNIVERSITY R&DB FOUNDATION, Seoul (KR)

(72) Inventors: Bum-Joon Kim, Seoul (KR); So-Young Lee, Incheon (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/761,933

(22) PCT Filed: Oct. 26, 2018

(86) PCT No.: PCT/KR2018/012812
§ 371 (c)(1),
(2) Date: May 6, 2020

(87) PCT Pub. No.: WO2019/088590
PCT Pub. Date: May 9, 2019

(65) Prior Publication Data
US 2020/0323928 A1  Oct. 15, 2020

(30) Foreign Application Priority Data

Nov. 6, 2017 (KR) .................... 10-2017-0146770

(51) Int. Cl.
*A61K 35/74* (2015.01)
*A61P 35/00* (2006.01)
*A61K 39/04* (2006.01)
*A61K 39/39* (2006.01)
*C12N 1/20* (2006.01)
*C12R 1/32* (2006.01)

(52) U.S. Cl.
CPC .............. *A61K 35/74* (2013.01); *A61K 39/04* (2013.01); *A61K 39/39* (2013.01); *A61P 35/00* (2018.01); *C12N 1/205* (2021.05); *C12R 2001/32* (2021.05)

(58) Field of Classification Search
None
See application file for complete search history.

(56) References Cited

FOREIGN PATENT DOCUMENTS

| JP | 2014-502256 A | 1/2014 | |
|---|---|---|---|
| KR | 10-2001-0033132 A | 4/2001 | |
| KR | 10-2016-0021933 A | 2/2016 | |
| KR | 10-2016-0093023 A | 8/2016 | |
| WO | WO-2016028028 A1 * | 2/2016 | ............. A61K 35/74 |

OTHER PUBLICATIONS

Translation of Kim et al (WO2016/028028, Feb. 25, 2016; IDS filed on May 6, 2020).*
International Search Report and Written Opinion forPCT/KR2018/012812 dated May 15, 2019, all pages.
Tortoli, E., "Microbiological Features and Clinical Relevance of New Species of the Genus *Mycobacterium*", Clinical Microbiology Reviews, 2014, vol. 27, No. 4, pp. 727-752. See entire document.
Fowler, et al., "Mycobacteria activate T-cell anti-tumour responses via cytokines from type 1 myeloid dendritic cells: a mechanism of action for cancer immunotherapy," Cancer Immunology, Immunotherapy, Apr. 2012 (electronic publication: Oct. 15, 2011), vol. 61, No. 4, pp. 535-547, <DOI: 10.1007/s00262-011-1121-4>. See abstract.
Chinmoy Mukherjee et al., "Total synthesis of an antigenic heptasaccharide motif found in the cell-wall lipooligosaccharide of *Mycobacterium gordonae* strain 989" DOI 10.1007/s10719-008-9107-y, Glycoconj J (2008) 25:611-624.

* cited by examiner

*Primary Examiner* — Brian Gangle
(74) *Attorney, Agent, or Firm* — Kilpatrick Townsend & Stockton LLP

(57) ABSTRACT

The present invention relates to an anti-cancer regulatory response and immunotherapy by *Mycobacterium paragordonae* (*M. paragordonae*). *Mycobacterium paragordonae* according to an aspect has cancer cytotoxicity mediated by natural killer cells or T cells as well as cytotoxicity against cancer cells, and inhibits activation of cancer cytotoxicity regulatory T cells of macrophages or dendritic cells to induce an immune response, thereby inhibiting tumor formation and thus being useful for a cancer immunotherapeutic agent.

11 Claims, 37 Drawing Sheets
Specification includes a Sequence Listing.

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Forward primer for mBcl2

<400> SEQUENCE: 1
acttcgcaga gatgtccagt ca                                                  22

<210> SEQ ID NO 2
<211> LENGTH: 18
<212> TYPE: DNA
<213> ORGANISM: Artificial Sequence
<220> FEATURE:
<223> OTHER INFORMATION: Reverse primer for mBcl2

<400> SEQUENCE: 2
tggcaaagcg tcccctc                                                        18

<210> SEQ ID NO 3
<211> LENGTH: 19
<212> TYPE: DNA
<213> ORGANISM: Artificial Sequence
<220> FEATURE:
<223> OTHER INFORMATION: Forward primer for mFoxP3

<400> SEQUENCE: 3
ggcccttctc caggacaga                                                      19

<210> SEQ ID NO 4
<211> LENGTH: 20
<212> TYPE: DNA
<213> ORGANISM: Artificial Sequence
<220> FEATURE:
<223> OTHER INFORMATION: Reverse primer for mFoxp3

<400> SEQUENCE: 4
gctgatcatg gctgggttgt                                                     20

<210> SEQ ID NO 5
<211> LENGTH: 20
<212> TYPE: DNA
<213> ORGANISM: Artificial Sequence
<220> FEATURE:
<223> OTHER INFORMATION: Forward primer for mIL-10
```

```
<400> SEQUENCE: 5
ccctttgcta tggtgtcctt                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for mIL-10

<400> SEQUENCE: 6
tggtttctct tcccaagacc                                              20

<210> SEQ ID NO 7
<211> LENGTH: 20
<212> TYPE: DNA
<213> ORGANISM: Artificial Sequence
<220> FEATURE:
<223> OTHER INFORMATION: Forward primer for mPerforin1

<400> SEQUENCE: 7
ctggctccca ctccaaggta                                              20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for mPerforin1

<400> SEQUENCE: 8
ggctgtaagh accgagatgc                                              20

<210> SEQ ID NO 9
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 9
atgccacagg attccatacc                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for mbeta-actin

<400> SEQUENCE: 10
gacggccagg tcatcactat                                              20
```

USE OF *MYCOBACTERIUM PARAGORDONAE* FOR CANCER IMMUNOTHERAPY

TECHNICAL FIELD

The present invention relates to an anti-cancer regulatory response and immunotherapy by *Mycobacterium paragordonae* (*M. paragordonae*).

BACKGROUND ART

Cancers as malignant tumors are occurring throughout the world differently from infectious diseases which occur only in particular areas. According to a report by WHO, approximately 14 million new cases of cancer were diagnosed worldwide and approximately 33 million patients are suffering from cancers in a single year of 2012, and 8.2 million patients died of cancer in that year. In Korea, it was reported in a research of 2011 that approximately 22 million people were diagnosed with cancer and there were approximately 110 million patients suffering from cancer. Also, it has been revealed that approximately 72,000 patients die of cancer, which is the number one cause of disease-induced death.

In order to treat a cancer, surgical excision is primarily required. However, there is a limitation in that the surgical operation is restricted according to the size and metastasis of cancer cells. A chemotherapy as an anti-cancer therapy that is most widely used at present has a limitation because a particular therapeutic agent for the chemotherapy can be applied to a particular cancer, and thus there is a need for development of therapeutic agents for various types of cancers, i.e., over 100 types of cancers. Moreover, since a cancer cell originates from a normal cell, the chemotherapy may act on normal cells as well, resulting in many side effects. An immunotherapy as another anti-cancer therapy is known to cause serious side effects, like chemotherapy, despite its advantage of being applied to various types of cancers. Given that cancers commonly occur in old patients, the side effects caused by such therapies may be a considerable burden on the patients, and it is not considered that life extension through treatment leads to improved quality of life. Therefore, a tumor immunotherapy that can be applied to various types of cancers and has reduced side effects is receiving a great deal of attention.

The tumor immunotherapy started based on the finding by Coley in 1891 that bacterial infection induces cancer patients' temporary recovery, and it was found in the 1960s that *Mycobacterium bovis* BCG (to be referred to as BCG hereinafter) eliminated some cancers. It is known that non-tuberculosis *mycobacteria* are excellent in immunity-inducing capability due to complex components of their cell walls, and thus the non-tuberculosis *mycobacteria* are used in research into therapeutic agents of various kinds of cancers (Table 1). Particularly, since BCG received FDA approval as an acceptable tumor immunotherapeutic agent for a bladder cancer in the 1990s, it has been used until now. It has been reported that use of BCG as a therapeutic agent reduces a recurrence rate over 40%. However, the BCG therapeutic agent is effective only for treatment of an early-stage bladder cancer, there have been reports on cases of considerable side effects. In addition, 90% of bladder cancer patients having been treated showed cystitis symptoms, a high fever was observed in 4% of the patients, and an infection-induced granuloma was unusually induced. When the BCG is used as a therapeutic agent for a lung cancer or a liver cancer, occurrences of serious side effects such as a high fever of 40° C. or liver dysfunction have been reported.

Accordingly, there is an ongoing need to develop novel immunotherapeutic agents for cancer treatment.

DESCRIPTION OF EMBODIMENTS

Technical Problems

An aspect is to provide an anti-cancer immunotherapy by *Mycobacterium paragordonae* and use thereof.

Another aspect is to provide a pharmaceutical composition for prevention or treatment of a cancer, comprising *Mycobacterium paragordonae* or a lysate or culture medium thereof as an effective ingredient.

Still another aspect is to provide a vaccine composition for immunotherapy of a cancer, which comprises *Mycobacterium paragordonae* or a lysate or culture medium thereof as an effective ingredient.

Still another aspect is to provide a health functional food composition for immunoregulation, comprising *Mycobacterium paragordonae* or a lysate or culture medium thereof as an effective ingredient.

Solutions to Problems

An aspect provides immunotherapy based *Mycobacterium paragordonae* and use thereof.

Another aspect provides a pharmaceutical composition for preventing or treating a cancer, which comprises *Mycobacterium paragordonae* or a lysate or culture medium thereof as an effective ingredient.

Still another aspect provides a vaccine composition for preventing or treating a cancer, which comprises *Mycobacterium paragordonae* or a lysate or culture medium thereof as an effective ingredient.

Still another aspect provides a method for preventing or treating a cancer, the method comprising administering to a subject a therapeutically effective amount of *Mycobacterium paragordonae* or a lysate or culture medium thereof.

Still another aspect provides a method for regulating the immunity of a subject, the method comprising administering to the subject a therapeutically effective amount of *Mycobacterium paragordonae* or a lysate or culture medium thereof.

Still another aspect provides use of *Mycobacterium paragordonae* or a lysate or culture medium thereof for preparing a pharmaceutical preparation for treating a cancer.

As used herein, the term "treat" may mean the cancer is cured within a short period of time relative to natural cure. The term "treat" may encompass prevention, amelioration and/or alleviation of cancer. In addition, the term "treat" may encompass all of treatments of cancer-related diseases.

As used herein, the term "pharmaceutically effective amount" or "effective ingredient" may mean an amount of a composition, which is sufficient to relieve a disease, a disorder, a condition, or one or more symptoms thereof, to suppress progression thereof or prevent used in the process of carrying out the invention provided in the present application, which is sufficiently effective in.

As used herein, the terms "administering," "applying," "introducing" and "implanting" are interchangeably used, and may mean arranging a composition according to an embodiment to a subject by a method or a route causing at least partial localization to a desired site.

As used herein, the term "anti-cancer" means all of prevention of a cancer, treatment thereof, and alleviation and relief of symptoms thereof, and the term "cancer" includes, but is not limited to, a solid cancer and a blood cancer.

Examples of cancers that can be treated by the present invention include, but are not limited to, cancer of the head, neck, eye, mouth, throat, esophagus, chest, bone, lung, colon, rectum, stomach, prostate, breast, ovaries, kidney, liver, pancreas, and brain. As used herein, the term "cancer" may further include primary cancer and metastatic cancer, unless otherwise indicated. Examples of the cancer may include lung cancer, pancreatic cancer, stomach cancer, liver cancer, colorectal cancer, brain cancer, breast cancer, thyroid cancer, bladder cancer, esophageal cancer, leukemia, ovarian cancer, melanoma, head and neck cancer, skin cancer, prostate cancer, rectal cancer, pancreatic cancer, hepatocellular cancer, or cervical cancer.

As used herein, the term "lysate" may mean a biological component in the *Mycobacterium paragordonae*, e.g., cell wall or membrane, or a component of a bacterial DNA, and fragments of useful components such as a culture broth containing metabolites exogenously released during cultivation of the *Mycobacterium paragordonae*. The lysate may be produced by sterilization (e.g., sterilization using moist heat), irradiation, pressure or ultrasonic crushing.

In a specific embodiment, the *Mycobacterium paragordonae* may be a vital bacterium or a dead bacterium. More specifically, the dead bacterium may be a dead bacterium resulting from heat treatment. The heat-treated *Mycobacterium* may be a non-pathogenic or inactivated *Mycobacterium paragordonae*.

In another specific embodiment, the *Mycobacterium paragordonae* may be a *Mycobacterium paragordonae* strain of Deposition No. KCTC 12628BP (Korea Research Institute of Bioscience & biotechnology), deposited Jul. 17, 2014, with the Korea Research Institute of Bioscience and Biotechnology (KRIBB), 181 Ipsin-gil, Jeongeup-si, Jeollabuk-do 56212, Republic of Korea.

In still another specific embodiment, the *Mycobacterium paragordonae*, or the lysate or culture medium thereof may be administered in combination with an anti-cancer agent. As used herein, the term "combination administration" may mean being concomitantly "together" or "concurrently" on the same day, and being "sequentially" or "separately" administered on different days. "Concurrent" administration may encompass being administered within about two hours or within a period of about less than one hour, as defined in the present application. "Separate" administration may encompass being administered at an interval of about 12 hours or more, about 8 hours or more, about 6 hours or more, about 4 hours or more, about 2 hours or more, as defined in the present application. "Sequential" administration may encompass administering *Mycobacterium paragordonae* and an anti-cancer agent at a plurality of fractions and/or doses and/or at different time points. Examples of the anti-cancer agent may include a platinum-based alkylating anti-cancer agent. Specifically, the platinum-based alkylating anti-cancer agent may be one or more selected from the group consisting of cisplatin, carboplatin, ormaplatin, oxaliplatin, Doxorubicin, geniplatin, enroplatin, lobaplatin, spiroplatin, tetraplatin, ormiplatin, and iproplatin.

Without being bound to a particular theory, the *Mycobacterium paragordonae* according to one embodiment may suppress the expression or activity of an apoptosis inhibitory factor (e.g., Bcl-2), or may enhance the expression or activity of a cytotoxicity factor (e.g., perforin and granzyme).

In addition, without being bound to a particular theory, the *Mycobacterium paragordonae* according to one embodiment may induce invasion of immune cells into tumor tissues. More specifically, the *Mycobacterium paragordonae* may regulate immonocytokines. In an example, the *Mycobacterium paragordonae* may suppress the expression or activity of interleukin (IL)-10, or may enhance the expression or activity of TNF-α, IFN-γ, IL-2, or IL-12.

In addition, without being bound to a particular theory, the *Mycobacterium paragordonae* according to one embodiment may have cancer cytotoxicity mediated by natural killer cells or T cells, or may enhance the cytotoxicity natural killer cells, macrophages or dendritic cells or may induce a humoral immune response.

In one embodiment, the *Mycobacterium paragordonae* may induce an immune response as well as cytotoxicity for a cancer cell itself owing to the advantages stated above, and thus can be advantageously used for a pharmaceutical composition or a vaccine composition for cancer immunotherapy.

The pharmaceutical composition or the vaccine composition may include a pharmaceutically acceptable carrier and/or additives. For example, the pharmaceutical composition or the vaccine composition may include sterile water, a physiological saline solution, a commonly used buffer (phosphate, citrate or other organic acids), a stabilizer, a salt, an antioxidant (ascorbic acid, etc.), a surfactant, a suspending agent, a tonicity agent, or a preservative. For topical administration, the pharmaceutical composition or the vaccine composition may also include a combination with an organic material such as a biopolymer or an inorganic material such as hydroxyapatite, specifically, a collagen matrix, a polylactate polymer or copolymer, a polyethyleneglycol polymer or copolymer, or a chemical derivative thereof.

The pharmaceutical composition according to one embodiment may appropriately include a suspending agent, a dissolving aid, a stabilizer, a tonicity agent, a preservative, an adsorption inhibitor, a surfactant, a diluent, an excipient, a pH adjuster, a pain-free agent, a buffering agent, a reducing agent, or an antioxidant according to the administration method or formulation thereof, as necessary. The pharmaceutically acceptable carrier and/or dosage forms suitably used in the present invention, including those listed above, are described in [Remington's Pharmaceutical Sciences, 19th ed., 1995] in greater detail. The pharmaceutical composition according to one embodiment may be formulated with the pharmaceutically acceptable carrier and/or excipient using a method which can be readily practiced by a person skilled in the art to which the present invention belongs, and then prepared in form of a unit dose or by being packed into a multi-dose container. In this case, the formulation may be in form of a solution in an oily or aqueous medium, a suspension or an emulsion, or in dosage form of powders, granules, tablets or capsules.

The composition may be formulated in an oral or parenteral dosage form. The oral dosage form may include granules, powders, solutions, tablets, capsules, dry syrups, or a combination thereof. The parenteral dosage form may be an injection or an external skin application. The external skin application may include a cream, a gel, an ointment, a skin emulsion, a suspension, a transdermal delivery patch, a drug-containing bandage, a lotion, or a combination thereof. The external skin application may be appropriately mixed, as necessary, with components such as typical cosmetics, medicines, or over the counter drugs used for external skin applications, for example, aqueous components, oleaginous components, powdery components, alcohols, moisturizers, thickeners, UV absorbers, skin whitening agents, antiseptics, antioxidants, surfactants, perfumes, coloring agents, a variety of skin nutrients, or any combination thereof. The external skin application may be appropriately mixed with metal sequestering agents such as disodium edetate, trisodium edetate, sodium citrate, sodium polyphosphate, sodium metaphosphate, or gluconic acid; caffeine, tannin, verapamyl, licorice extract, glabridin, hot water extract of cauline fruits, and other galenicals; medicinal agents such as tocopherol acetate, glycyrrhizic acid, tranexamic acid, or a derivative or salt of any of the foregoing; vitamin C, ascorbic acid magnesium phosphate, ascorbic acid glucoside, arbutin, and kojic acid; and sugars such as glucose, fructose, or trehalose.

In addition, the vaccine composition may include an adjuvant, specifically an arbitrary material or compound capable of promoting or increasing a T cell mediated response. In one or more one embodiment, the adjuvant may be used when chemically or thermally killed bacteria are included in the composition. The adjuvant is known in the art, and usable examples thereof may include aluminum hydroxide, aluminum phosphate, aluminum potassium sulfate, crosslinked polyacrylic acid polymer, dimethyldioctadecyl-ammonium bromide (DDA), immunomodulator, lactoferrin, or IFN-gamma inducer. In an embodiment, the crosslinked polyacrylic acid polymer may include Carbopol® homopolymer or copolymer, the immunomodulator may include IFN-gamma, IL-1, IL-2 or IL-12, and the IFN-gamma inducer may include poly I:C. In a specific embodiment, the aluminum hydroxide, the aluminum phosphate, or the aluminum potassium sulfate as a synthesized sugar polymer, may be contained in an amount of about 0.05% to about 0.1% by weight, and the crosslinked polyacrylic acid polymer may be contained in an amount of about 0.25% by weight.

The amount of *Mycobacterium paragordonae* administered may be an amount enough to induce a defensive immune response in a patient so as to allow the immune system of the patient to load an effective immune response against a cancer or a tumor. In certain embodiments of this specification, the number of *Mycobacteria paragordonae* may be $10^3$ to $10^{11}$, $10^4$ to $10^{10}$, $10^6$ to $10^{10}$, or $10^6$ to $10^9$. As another example, the dose of the *Mycobacterium paragordonae* provided as a suspending agent or a dry formulation may be 0.01 mg to 10 mg or 0.1 mg to 1 mg. As still another example, the dose may be $1 \times 10^3$ to $1 \times 10^{11}$ cfu/ml, $1 \times 10^4$ to $1 \times 10^{10}$ cfu/ml, $1 \times 10^6$ to $1 \times 10^{10}$ cfu/ml, or $1 \times 10^6$ to $1 \times 10^9$ cfu/ml.

Another aspect provides a health functional food composition for immunoregulatory activity, which comprises *Mycobacterium paragordonae* or a lysate or culture medium thereof as an effective ingredient.

The health functional food may be used for preventing or improving a cancer by immunoregulation (for example, immunity enhancement).

The health functional food composition may use *Mycobacterium paragordonae* or a lysate or culture medium thereof alone or in combination with other foods or food ingredients, and may be appropriately used by a general method. The amounts of effective ingredient mixed may be appropriately determined according to the purpose of use (prevention, health or therapeutic treatment). The composition of the invention may be generally added in an amount of 15 parts by weight or less per 100 parts by weight of the raw material of the composition at the time of manufacturing food or beverage. The kind of health functional food is not particularly limited. Among various kinds of the health functional food, a beverage composition may generally include various kinds of flavoring agents or natural carbohydrates, like ordinary beverages. The natural carbohydrate are monosaccharides such as glucose or fructose, disaccharides such as maltose or sucrose, polysaccharides such as dextrin or cyclodextrin, and sugar alcohols such as xylitol, sorbitol, or erythritol. As a sweetener, a natural sweetener such as thaumatine, stevia extract, or a synthetic sweetener such as saccharin or aspartame, may be used. The health functional food composition may also contain nutrients, vitamins, minerals (electrolytes), flavors, coloring agents, pectic acid and its salts, alginic acid and its salts, organic acids, protective colloid thickeners, pH control agents, stabilizers, antiseptics, glycerins, alcohols, carbonating agents for use in carbonated beverage, and a combination thereof. The health functional food composition may also contain natural fruit juices and fruit pulps for preparation of fruit juice drinks and vegetable drink, or a combination thereof.

BRIEF DESCRIPTION OF DRAWINGS

*Mycobacterium paragordonae* according to an aspect has cancer cytotoxicity mediated by natural killer cells or T cells as well as cytotoxicity against cancer cells, and inhibits activation of cancer cytotoxicity regulatory T cells of macrophages or dendritic cells to induce an immune response, thereby inhibiting tumor formation and thus being useful for a cancer immunotherapeutic agent.

Brief Description of Drawings

Figure 1A:
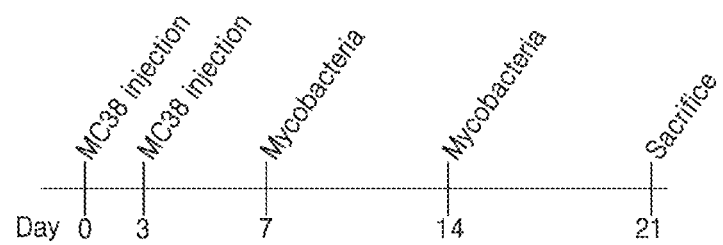

FIG. 1A is a diagram showing a dosing regimen of administering *Mycobacterium paragordonae* according to one embodiment to animal models.

Figure 1B:
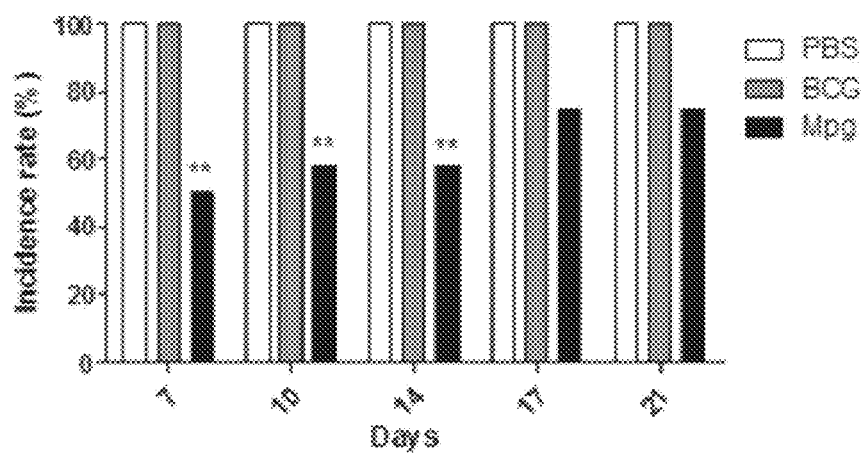

FIG. 1B is a graph showing incidence rates of cancer by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

Figure 1C:
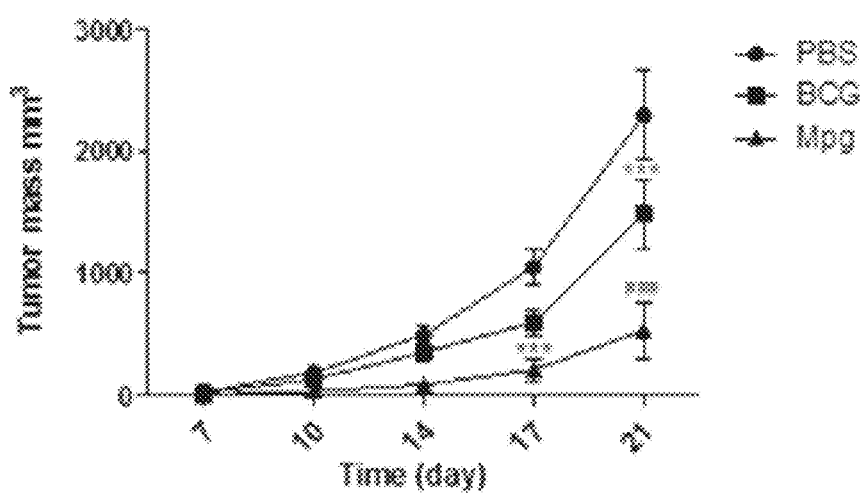

FIG. 1C is a graph showing changes in tumor size by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

Figure 1D:
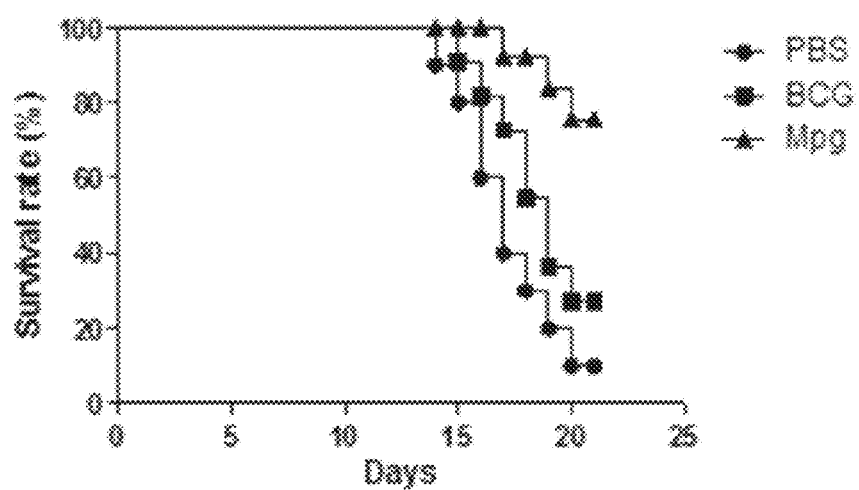

FIG. 1D is a graph showing survival rates by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

Figure 1E:
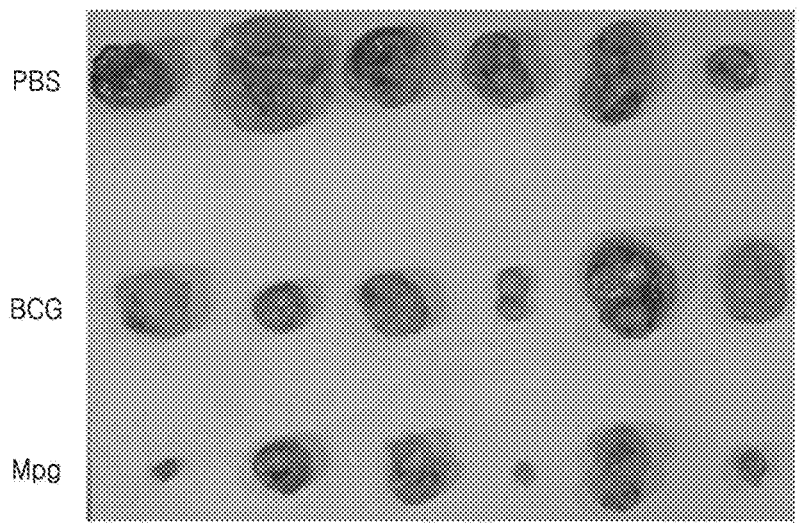

FIG. 1E shows changes in tumor size by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

Figure 2A:
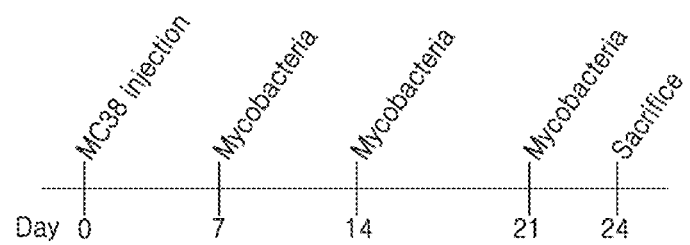

FIG. 2A is a diagram showing a dosing regimen of administering *Mycobacterium paragordonae* according to one embodiment to animal models.

Figure 2B:
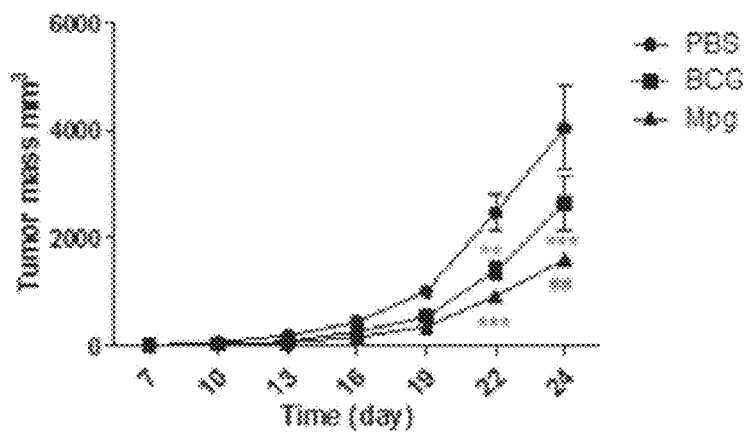

FIG. 2B is a graph showing changes in tumor size following tumor formation, by administration of *Mycobacterium paragordonae* according to one embodiment, where Mpg stands for *Mycobacterium paragordonae*; BCG stands for *Mycobacterium bovis* BCG; and PBS is a negative control.

Figure 2C:
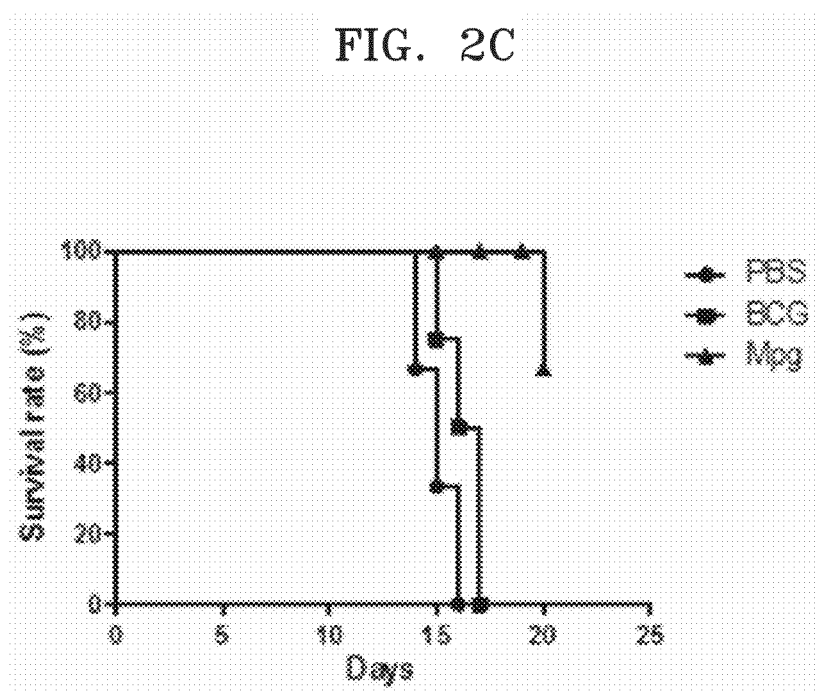

FIG. 2C is a graph showing survival rates following tumor formation, by administration of *Mycobacterium paragordonae* according to one embodiment, where Mpg stands for *Mycobacterium paragordonae*; BCG stands for *Mycobacterium bovis* BCG; and PBS is a negative control.

Figure 2D:
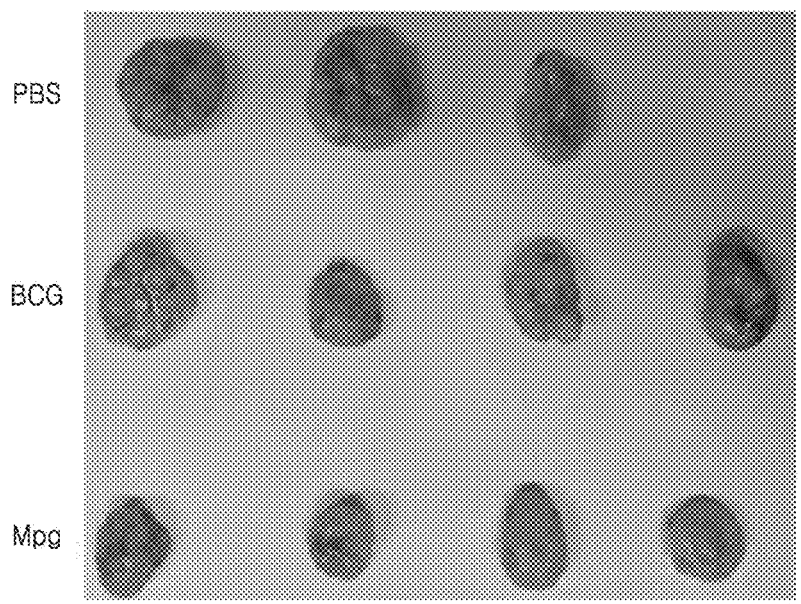

FIG. 2D shows changes in tumor size following tumor formation, by administration of *Mycobacterium paragordo-* nae according to one embodiment, where Mpg stands for *Mycobacterium paragordonae*; BCG stands for *Mycobacterium bovis* BCG; and PBS is a negative control.

Figure 2E:
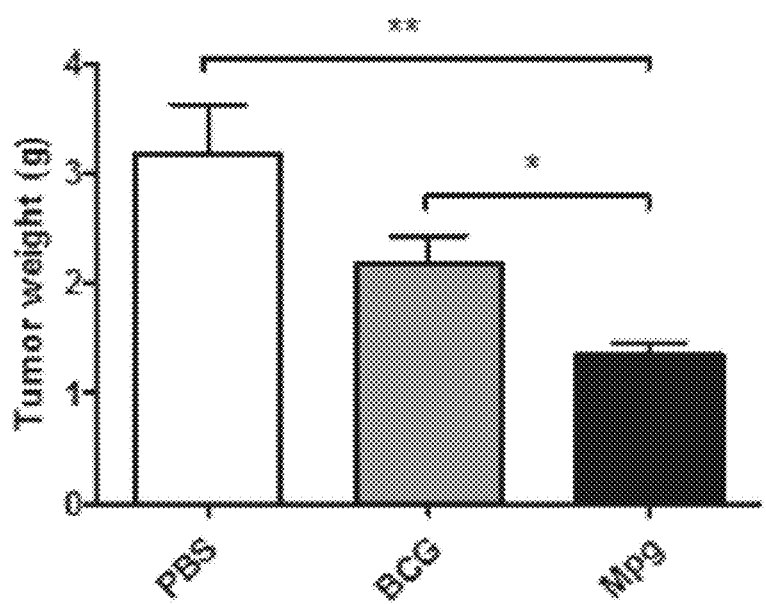

FIG. 2E shows tumor weights measured at 24 days following tumor formation, by administration of *Mycobacterium paragordonae* according to one embodiment, where Mpg stands for *Mycobacterium paragordonae*; BCG stands for *Mycobacterium bovis* BCG; and PBS is a negative control.

Figure 3A:
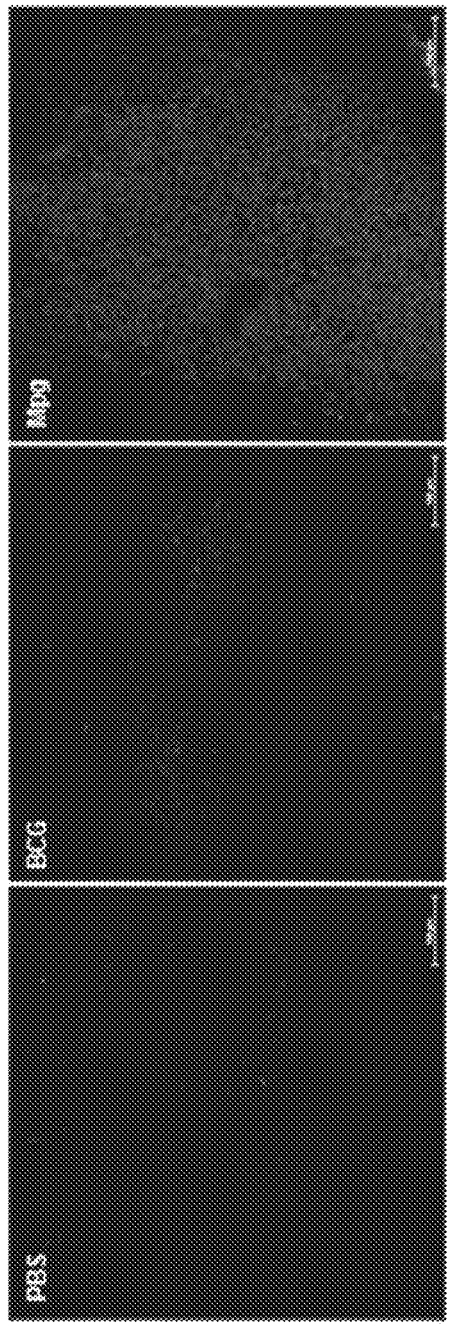

FIG. 3A shows the results of tumor cell apoptosis (the left panel), by administration of *Mycobacterium paragordonae* according to one embodiment, as determined by TUNEL assay, where Mpg stands for *Mycobacterium paragordonae*; BCG stands for *Mycobacterium bovis* BCG; and PBS is a negative control.

Figure 3B:
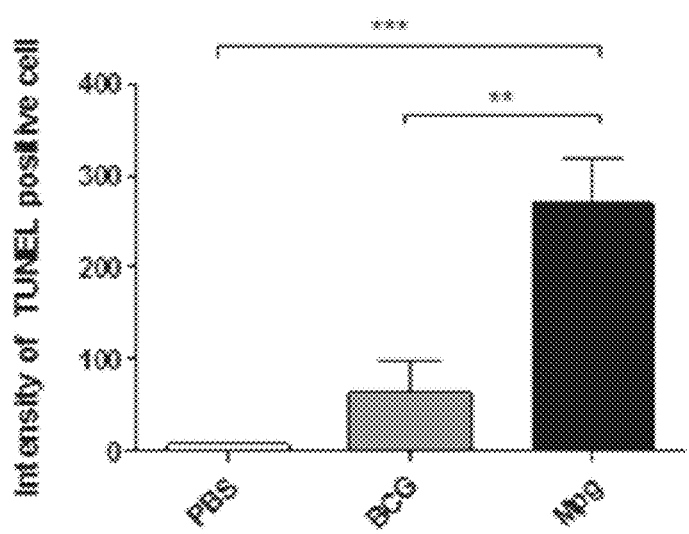

FIG. 3B is a graph showing the quantification results of apoptotic tumor cells, by administration of *Mycobacterium paragordonae* according to one embodiment, as determined by TUNEL assay, where Mpg stands for *Mycobacterium paragordonae*; BCG stands for *Mycobacterium bovis* BCG; and PBS is a negative control.

Figure 3C:
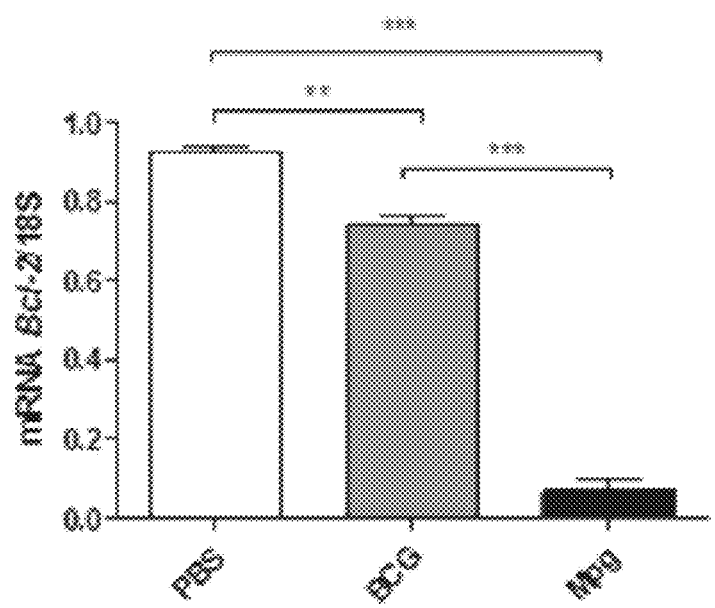

FIG. 3C is a graph showing the inhibited expression of Bcl-2 by administration of *Mycobacterium paragordonae* according to one embodiment, where Mpg stands for *Mycobacterium paragordonae*; BCG stands for *Mycobacterium bovis* BCG; and PBS is a negative control.

Figure 3D:
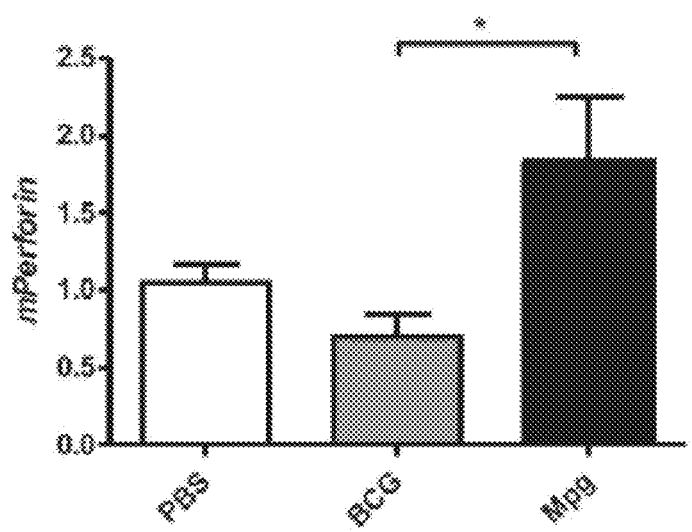

FIG. 3D is a graph showing the increased expression of perforin by administration of *Mycobacterium paragordonae* according to one embodiment, where Mpg stands for *Mycobacterium paragordonae*; BCG stands for *Mycobacterium bovis* BCG; and PBS is a negative control.

Figure 3E:
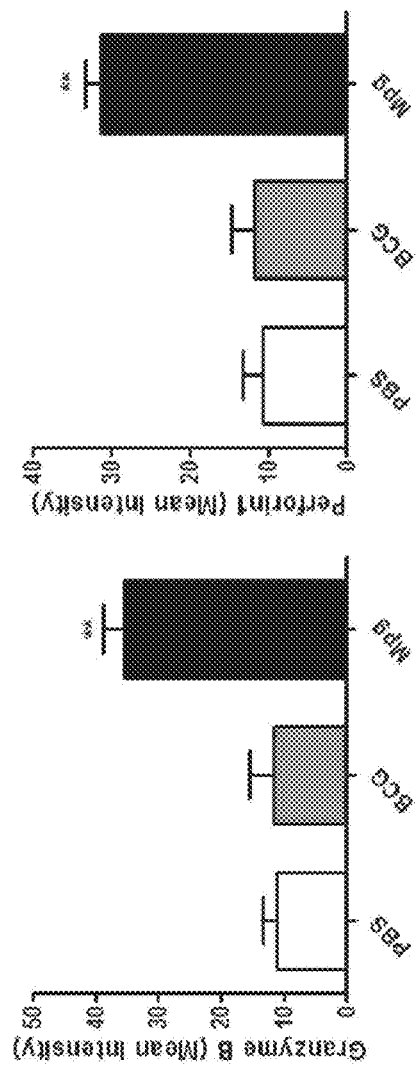

FIG. 3E shows the expression levels of perforin and granzyme by administration of *Mycobacterium paragordonae* according to one embodiment, as determined by IHC assay, where Mpg stands for *Mycobacterium paragordonae*; BCG stands for *Mycobacterium bovis* BCG; and PBS is a negative control.

Figure 4A:
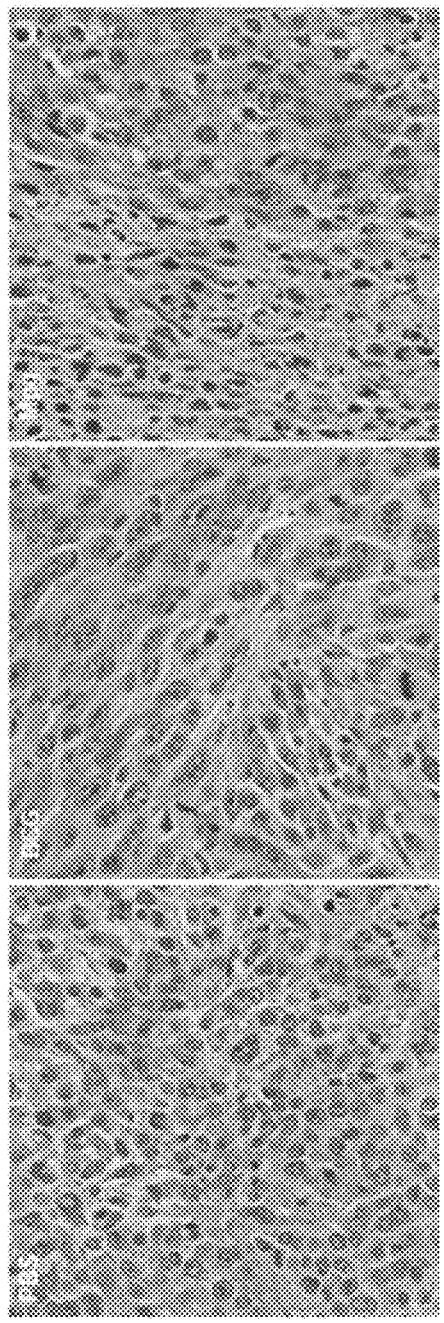

FIG. 4A shows the results of tumor cell apoptosis, by administration of *Mycobacterium paragordonae* according to one embodiment, as determined by H&E staining, where Mpg stands for *Mycobacterium paragordonae*; BCG stands for *Mycobacterium bovis* BCG; and PBS is a negative control.

Figure 4B:
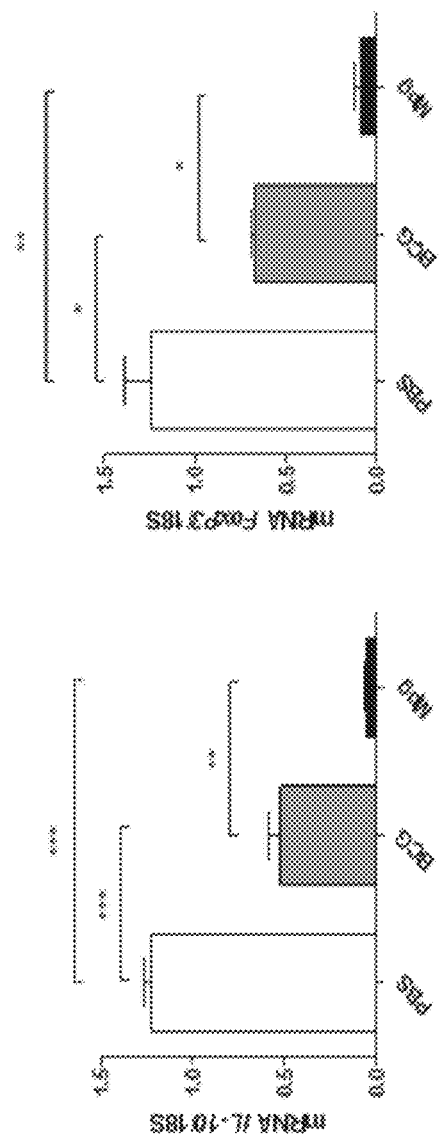

FIG. 4B is a graph showing the expression levels of IL-10 and FoxP3 by administration of *Mycobacterium paragordonae* according to one embodiment, as determined by quantitative real time PCR, where Mpg stands for *Mycobacterium paragordonae*; BCG stands for *Mycobacterium bovis* BCG; and PBS is a negative control.

Figure 4C:
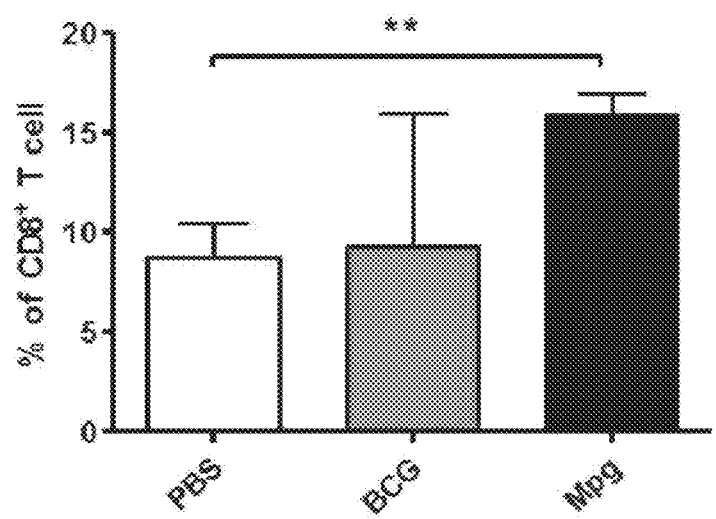

FIG. 4C shows the number of CD8 T cells in tumor tissues by administration of *Mycobacterium paragordonae* according to one embodiment, as determined by IHC assay, where Mpg stands for *Mycobacterium paragordonae*; BCG stands for *Mycobacterium bovis* BCG; and PBS is a negative control.

Figure 4D:
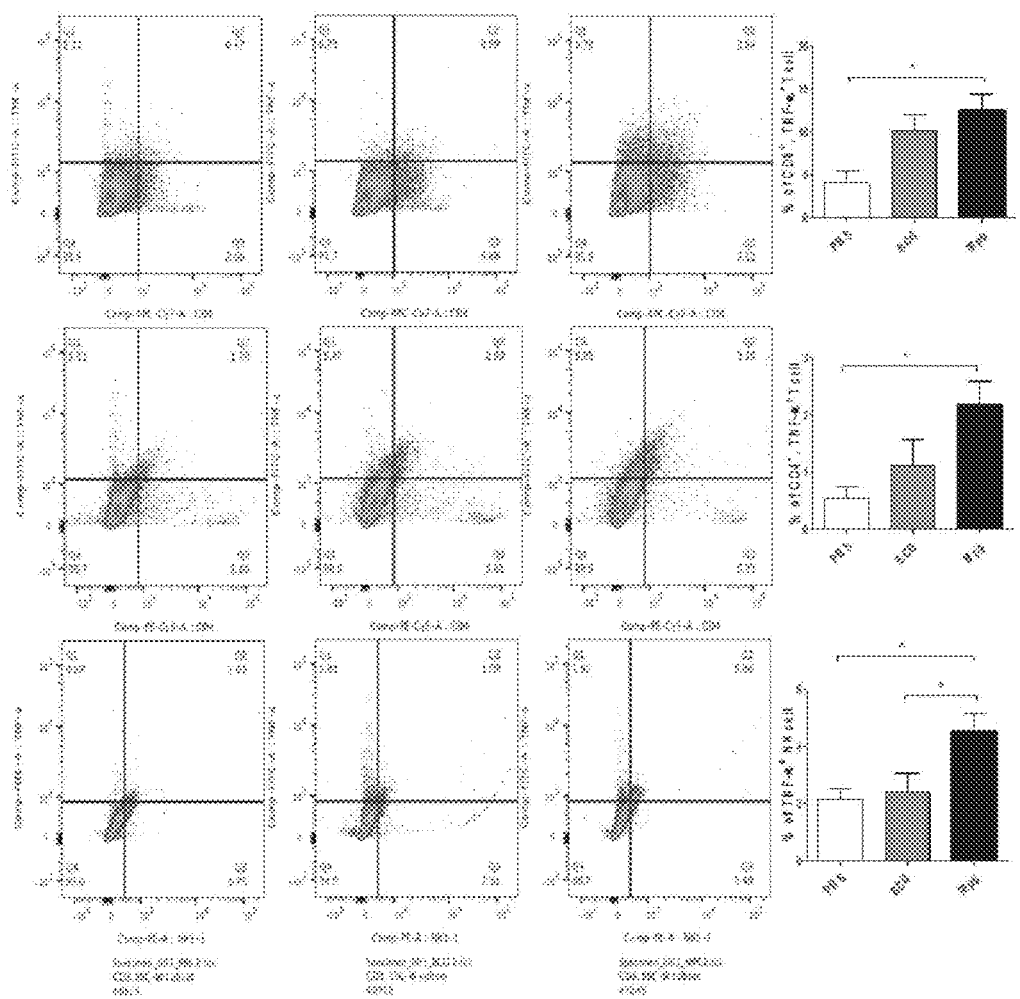

FIG. 4D shows proportions of TNF-α expressing CD4 and CD8 T cells and natural killer cells in tumors by stimulation with *Mycobacterium paragordonae* according to one embodiment, as determined by flow cytometry, where Mpg stands for *Mycobacterium paragordonae*; BCG stands for *Mycobacterium bovis* BCG; and PBS is a negative control.

Figure 4E:
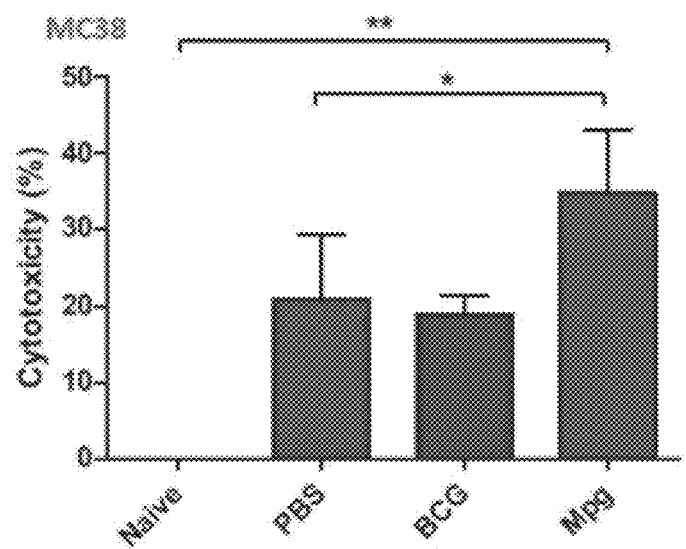

FIG. 4E is a graph showing the cell mediated toxicity by administration of *Mycobacterium paragordonae* according to one embodiment, where Mpg stands for *Mycobacterium paragordonae*; BCG stands for *Mycobacterium bovis* BCG; and PBS is a negative control.

Figure 4F:
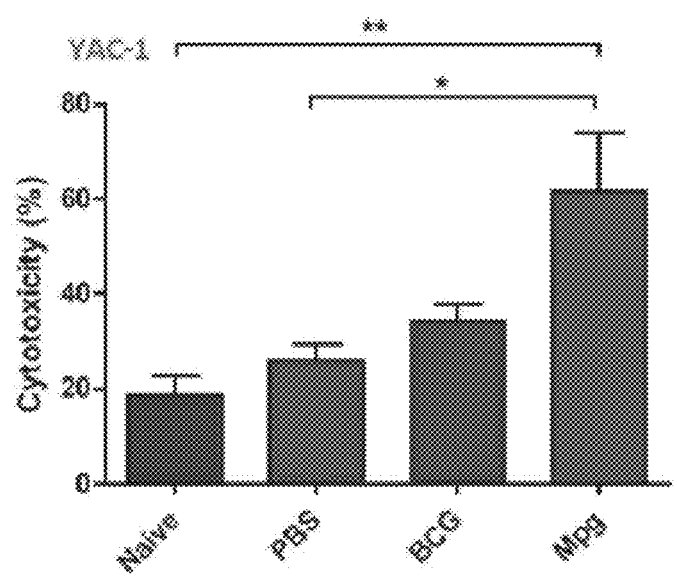

FIG. 4F is a graph showing the cytotoxicity of NK cells by administration of *Mycobacterium paragordonae* according to one embodiment, where Mpg stands for *Mycobacterium paragordonae*; BCG stands for *Mycobacterium bovis* BCG; and PBS is a negative control.

Figure 4G:
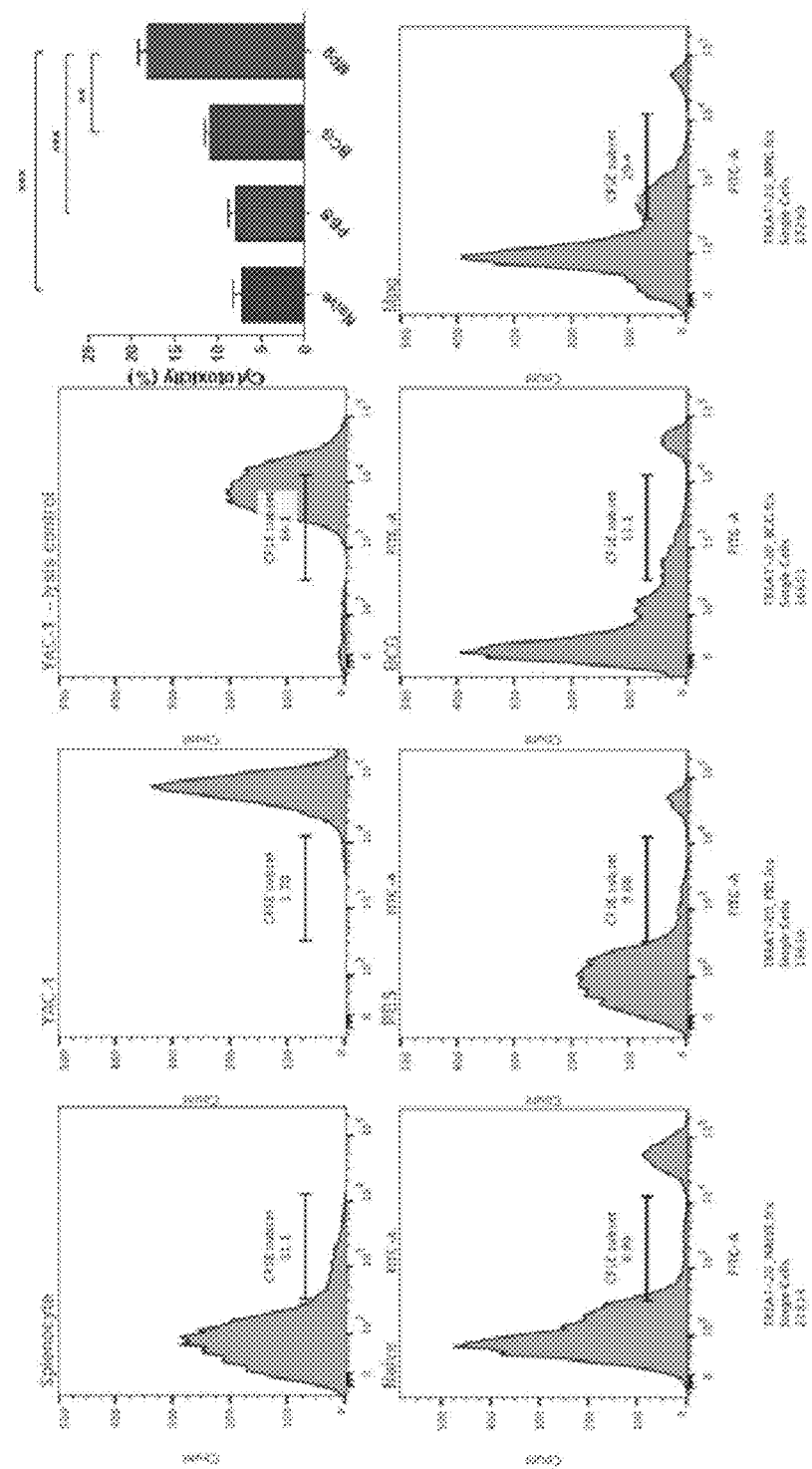

FIG. 4G is a graph showing the cytotoxicity of NK cells by administration of *Mycobacterium paragordonae* according to one embodiment, as determined by flow cytometry, where Mpg stands for *Mycobacterium paragordonae*; BCG stands for *Mycobacterium bovis* BCG; and PBS is a negative control.

Figure 5A:
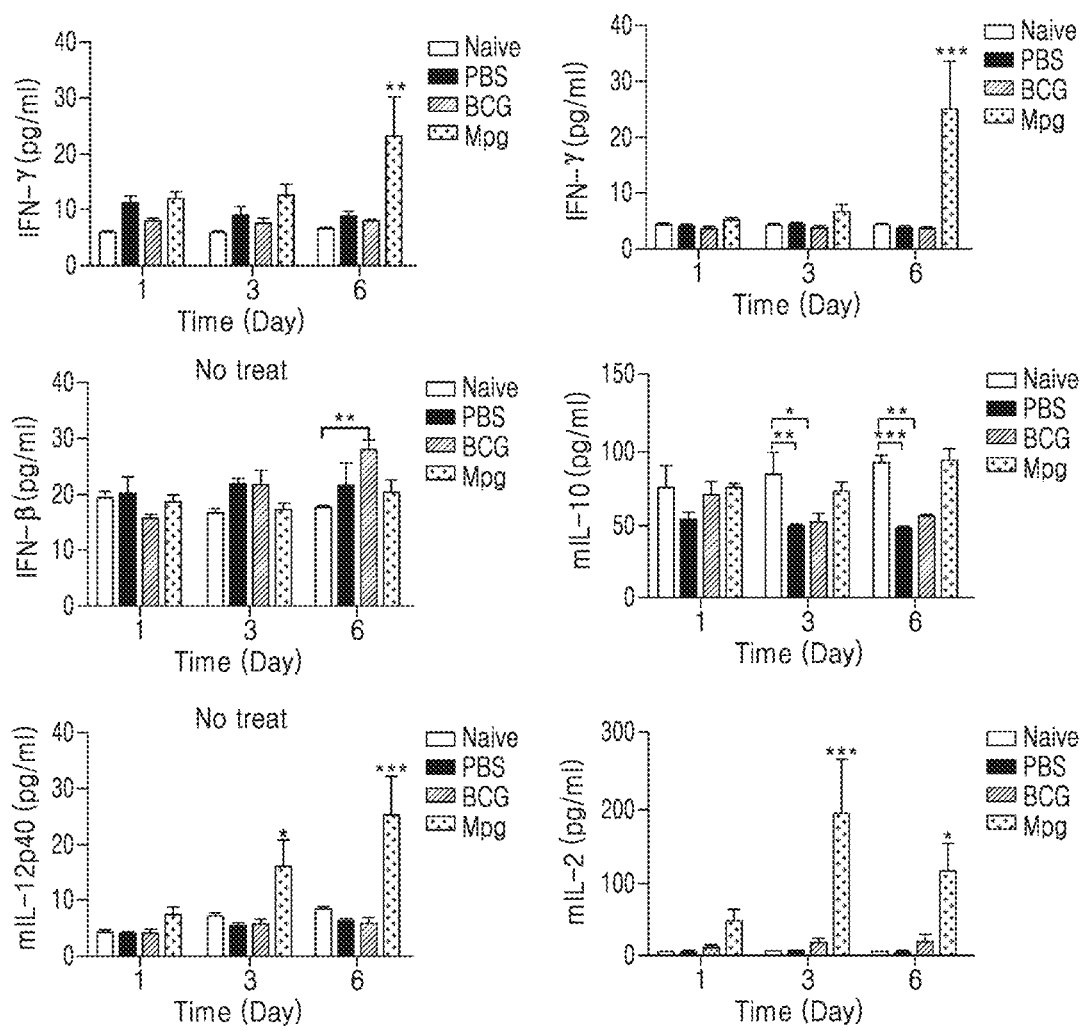

FIG. 5A shows the production of various inflammatory cytokines from spleen cells by stimulation with *Mycobacterium paragordonae* according to one embodiment, where Mpg stands for *Mycobacterium paragordonae*; BCG stands for *Mycobacterium bovis* BCG; and PBS is a negative control.

Figure 5B:
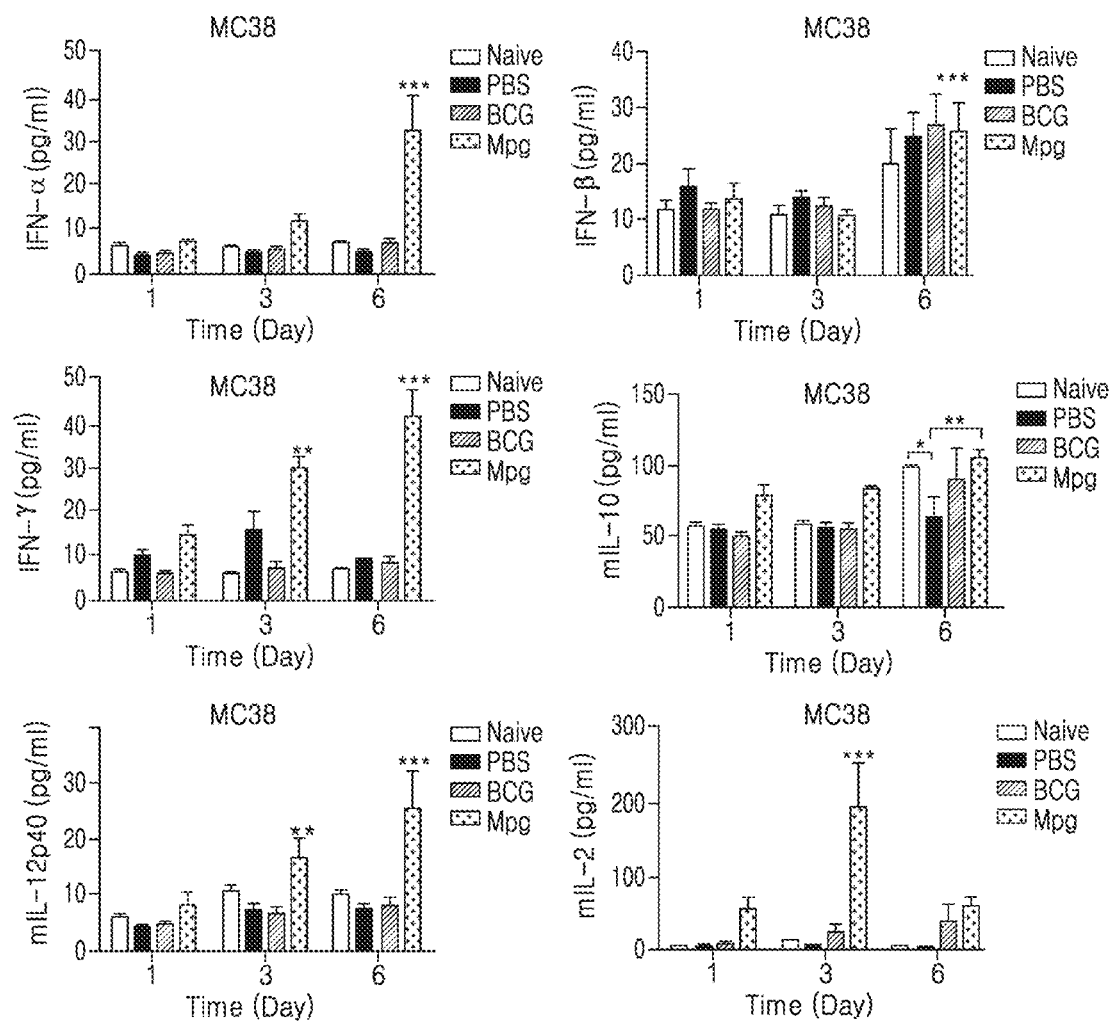

FIG. 5B shows the production of inflammatory cytokines secreted by stimulating spleen cells with *Mycobacterium paragordonae* according to one embodiment and then restimulating the spleen cells with MC38 tumor cell antigen, where Mpg stands for *Mycobacterium paragordonae*; BCG stands for *Mycobacterium bovis* BCG; and PBS is a negative control.

Figure 5C:
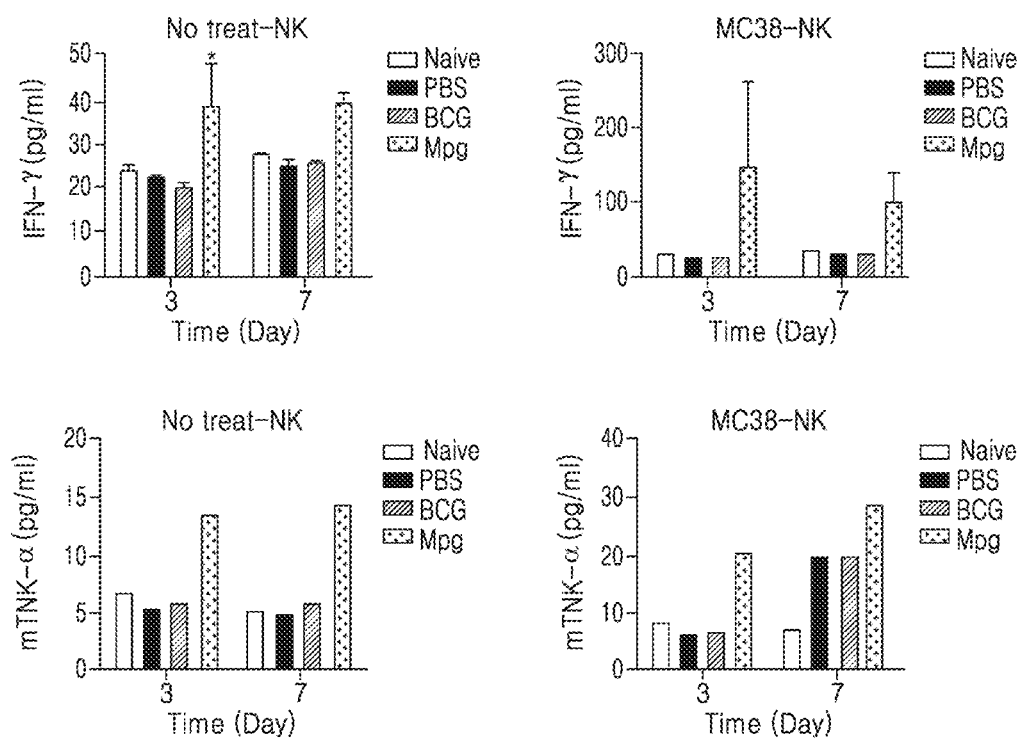

FIG. 5C shows production of inflammatory cytokines from natural killer cells in spleen cells by stimulation with *Mycobacterium paragordonae* according to one embodiment, where Mpg stands for *Mycobacterium paragordonae*; BCG stands for *Mycobacterium bovis* BCG; and PBS is a negative control.

Figure 5D:
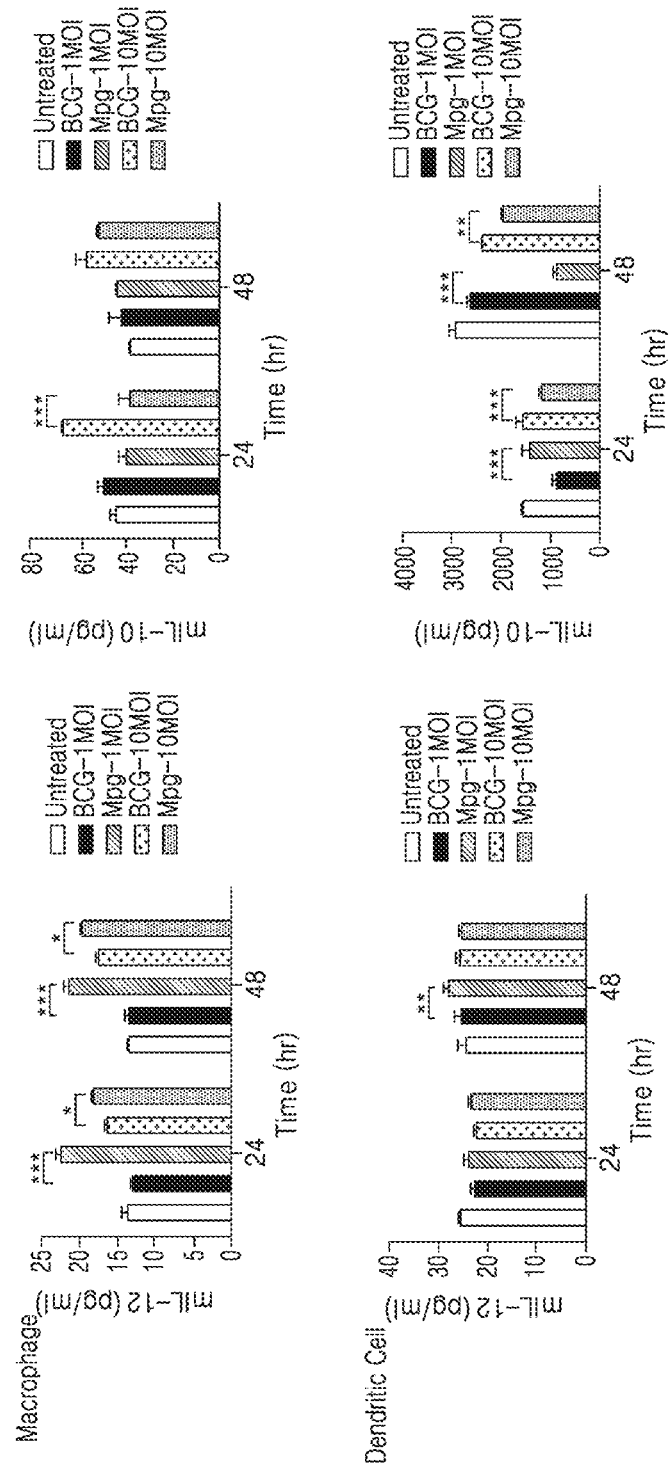

FIG. 5D is a graph showing the secretion of IL-12 and IL-10 in a macrophage (J774A.1) and a dendritic cell (DC.24) by treatment with *Mycobacterium paragordonae* according to one embodiment, where Mpg stands for *Mycobacterium paragordonae*; BCG stands for *Mycobacterium bovis* BCG; and PBS is a negative control.

Figure 5E:
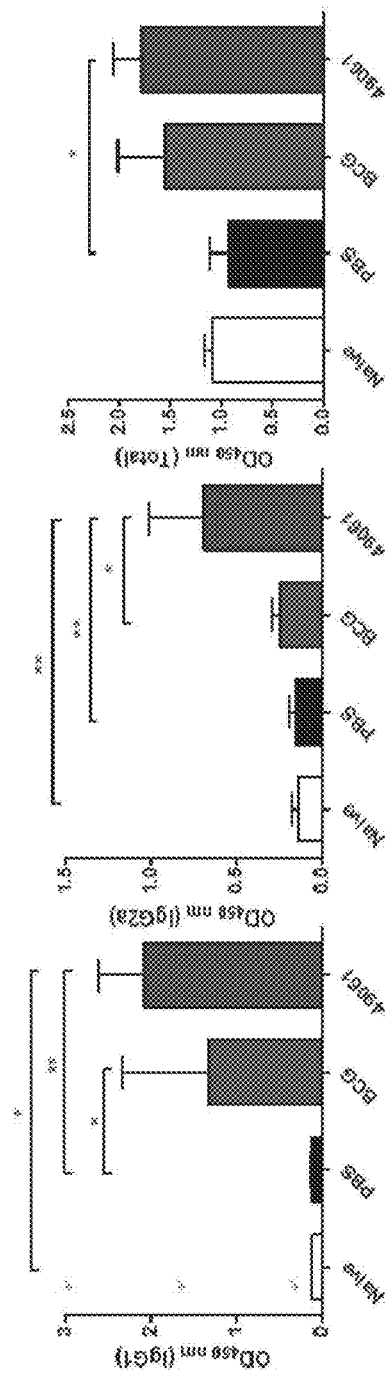

FIG. 5E shows proportions of IgG1, IgG2a, and total IgG in serums by stimulation with *Mycobacterium paragordonae* according to one embodiment, where Mpg stands for *Mycobacterium paragordonae*; BCG stands for *Mycobacterium bovis* BCG; and PBS is a negative control.

Figure 5F:
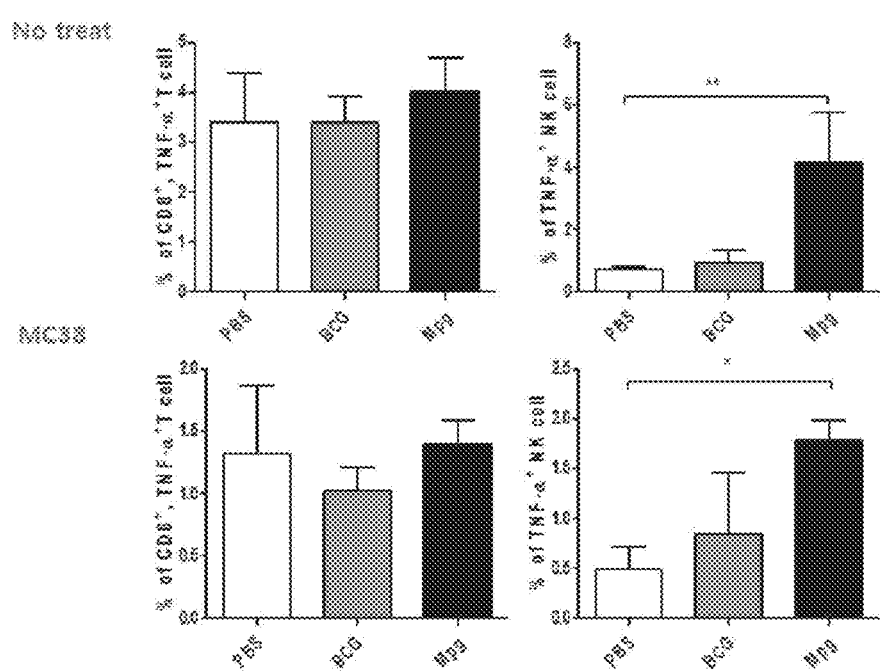

FIG. 5F shows proportions of TNF-α expressing CD8 T cells in spleen cells and natural killer cells by stimulation with *Mycobacterium paragordonae* according to one embodiment, as determined by flow cytometry, where Mpg stands for *Mycobacterium paragordonae*; BCG stands for *Mycobacterium bovis* BCG; and PBS is a negative control.

Figure 6A:
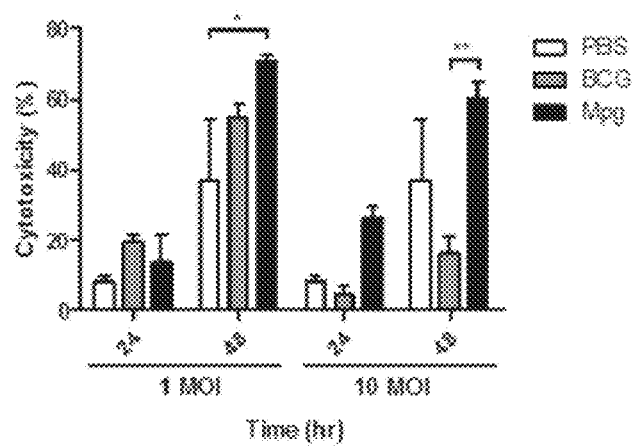

FIG. 6A is a graph showing the cytotoxicity of a macrophage (J774A.1) for an MC38 colorectal cancer by treatment with *Mycobacterium paragordonae* according to one embodiment, where Mpg stands for *Mycobacterium paragordonae*; BCG stands for *Mycobacterium bovis* BCG; and PBS is a negative control.

Figure 6B:
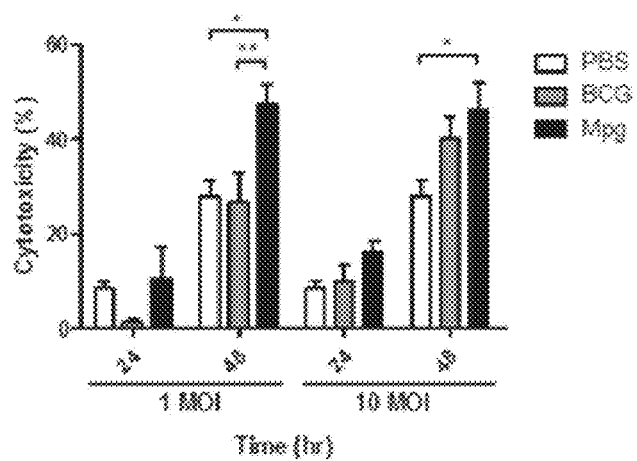

FIG. 6B is a graph showing the cytotoxicity of a dendritic cell (DC.24) for an MC38 colorectal cancer cell by treatment with *Mycobacterium paragordonae* according to one embodiment, where Mpg stands for *Mycobacterium paragordonae*; BCG stands for *Mycobacterium bovis* BCG; and PBS is a negative control.

Figure 6C:
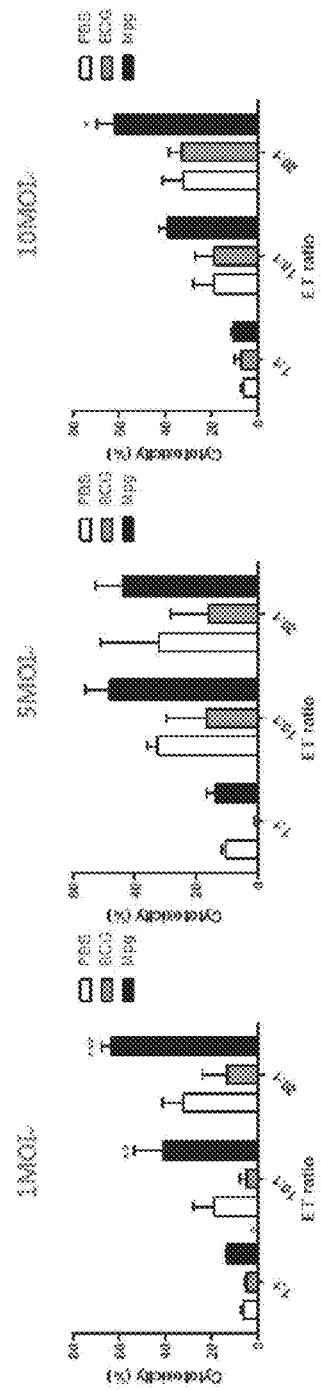

FIG. 6C is a graph showing the cytotoxicity of a macrophage (J774A.1) for an A549 lung cancer cell line by treatment with *Mycobacterium paragordonae* according to one embodiment, where Mpg stands for *Mycobacterium paragordonae*; BCG stands for *Mycobacterium bovis* BCG; and PBS is a negative control.

Figure 6D:
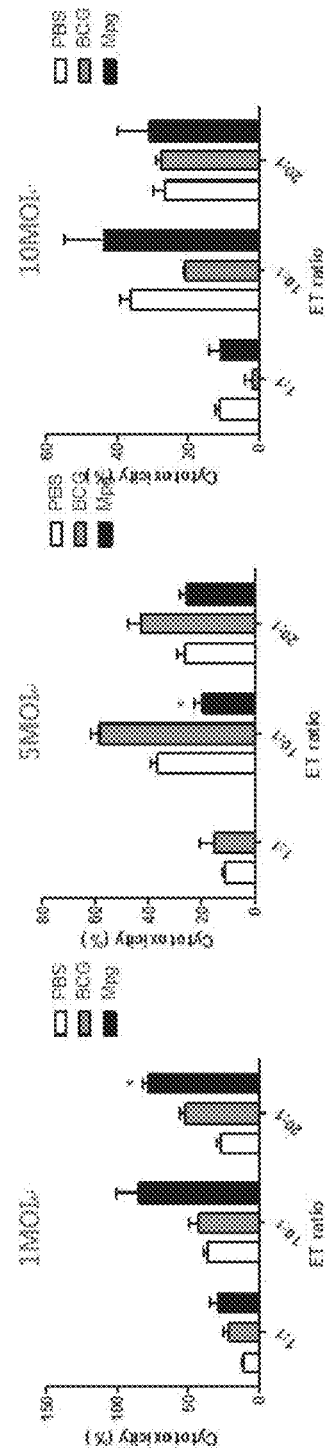

FIG. 6D is a graph showing the cytotoxicity of a macrophage (J774A.1) for an HepG2 liver cancer cell line by treatment with *Mycobacterium paragordonae* according to one embodiment, where Mpg stands for *Mycobacterium paragordonae*; BCG stands for *Mycobacterium bovis* BCG; and PBS is a negative control.

Figure 6E:
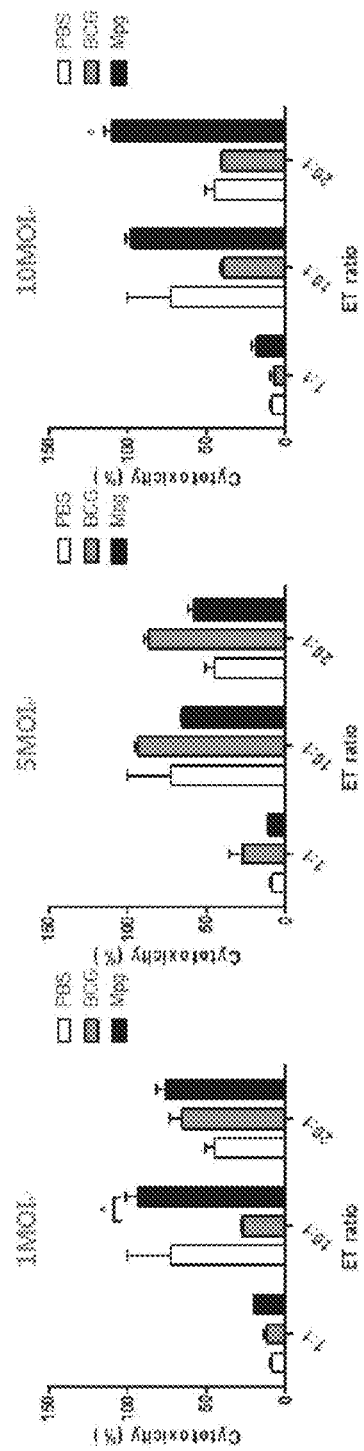

FIG. 6E is a graph showing the cytotoxicity of a macrophage (J774A.1) for an Mbt-2 bladder cancer cell line by treatment with *Mycobacterium paragordonae* according to one embodiment, where Mpg stands for *Mycobacterium paragordonae*; BCG stands for *Mycobacterium bovis* BCG; and PBS is a negative control.

Figure 6F:
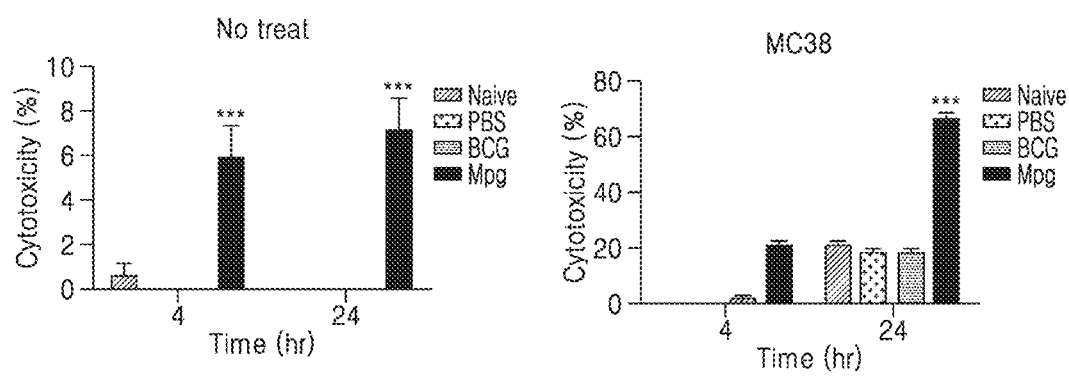

FIG. 6F is a graph showing the cytotoxicity of the cell culture medium of mouse spleen cells for murine colorectal cancer cell line MC38 by treatment with *Mycobacterium paragordonae* according to one embodiment, where Mpg stands for *Mycobacterium paragordonae*; BCG stands for *Mycobacterium bovis* BCG; and PBS is a negative control.

Figure 7A:
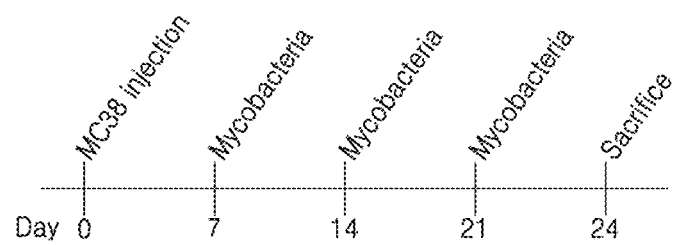

FIG. 7A is a diagram showing a dosing regimen of administering *Mycobacterium paragordonae* according to one embodiment to animal models to identify the effect of combination administration.

Figure 7B:
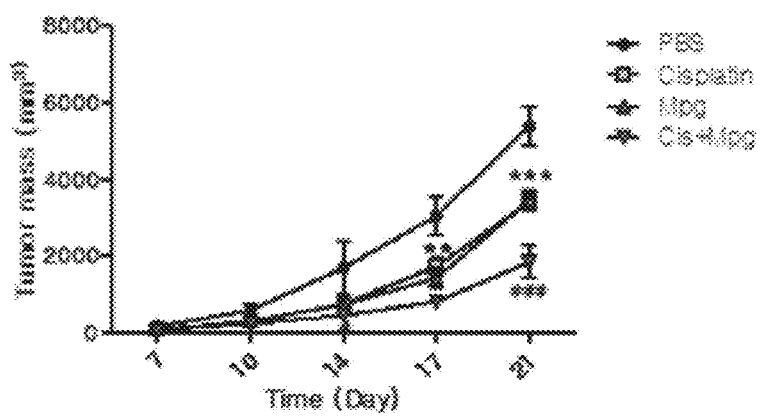

FIG. 7B is a graph showing changes in tumor size by administration of *Mycobacterium paragordonae* according to one embodiment, to identify the effect of combination administration, where Mpg stands for *Mycobacterium paragordonae*; Cis+Mpg stands for Cisplatin and *Mycobacterium paragordonae* administered in combination; Cisplatin stands for Cisplatin administered alone; and PBS is a negative control.

Figure 7C:
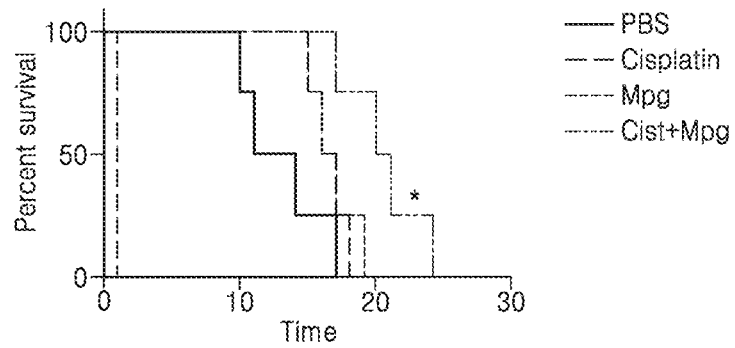

FIG. 7C is a graph showing survival rates by administration of *Mycobacterium paragordonae* according to one embodiment, to identify the effect of combination administration, where Mpg stands for *Mycobacterium paragordonae*; Cis+Mpg stands for Cisplatin and *Mycobacterium paragordonae* administered in combination; Cisplatin stands for Cisplatin administered alone; and PBS is a negative control.

MODE OF DISCLOSURE

Hereinafter, various embodiments will be presented for a better understanding of the present invention. However, the following embodiments are for illustrative purpose only, and are not intended to limit the scope of the present invention.

Reference Example 1. Cell Line Culture

The murine colorectal cancer cell line MC38 and the human breast cancer cell line MCF-7 were cultured using DMEM (Hyclon) culture media, and the murine macrophage cell line J774.1A (American Type Culture Collection, Manassa, Va., USA), the murine dendritic cells line DC2.4, and human liver cancer cell line Huh7, lung cancer cell line A549 and bladder cancer cell line Mbt-2 were cultured using RPM11640 (Hyclon) culture media. 10% fetal bovine serum (Invitrogen, USA), 2 mmol/ml of L-glutamine, 100 ug/ml of penicillin and 100 units/ml of streptomycin were added to the two culture media and cultured at 37° C. in a 5% $CO_2$ incubator.

Reference Example 2. Manufacture of Tumor Animal Model and Tumor Size Assay

Tumor formation was induced by injecting $1×10^6/100$ µl of colorectal cancer MC38 cell lines to right hind legs of 7-week old C57BL/6 female mice. $1×10^8/100$ µl of thermally inactivated *Mycobacterium paragordonae* was subcutaneously injected into the vicinity of the lymph node three times at an interval of three days. To comparatively investigate the anti-cancer effects, *Mycobacterium bovis* BCG currently being used for immunotherapy was used as a positive control, and PBS was used as a negative control. In addition, in order to confirm the combination administration effect, Cisplatin (50 µg/kg) was intraperitoneally administered. The sizes of formed tumors were measured twice a week, and tumor size measurements were converted to cubic millimeter tumor volumes using the formula below: $width^2×length×0.52$. After completion of the experiment, tumors were isolated from the mice, and some of the isolated tumors were fixed in 4% formalin solution and dissected to a thickness of 5-10 µm to then be stored in paraffin.

Reference Example 3. TUNEL Assay

To assay tumor cell apoptosis, DNA fragments were detected by terminal deoxynucleotidyl transferase-mediated dUTP nick-end labeling (TUNEL) assay. Fragmented tumor tissues were deparaffinized in xylene, and dead cells were stained using an ApopTag Peroxidase In Situ Apoptosis Detection Kit (Millipore) according to manufacturers instructions. Stained apoptotic cells were evaluated by confocal A1 microscope (NIKON, 136 Japan), and fluorescence was assayed using imaging software (NIS Elements Viewer 137 program).

Reference Example 4. Histological Analysis

The dissected tumors were fixed in 10% neutral buffered formalin and stored in paraffin. Paraffin-embedded blocks were cut into 5 µm fragments, which were stained with H&E, and immunohistochemistry (IHC) assay was performed on CD8 (1:100, eBioscience), granzyme B, and perforin (1:100, Santa Cruz). Digital images of slides were taken using Aperio Scanscope (Leica Microsystems), and stained antigens were quantified using HistoQuest software (version 6.0.1.116, TissueGnostics, Austria).

Reference Example 5. Assay for mRNA Expression Through Real Time PCR

For gene expression assay under tumor environments, quantitative real time PCR was performed. Total mRNAs were extracted from tumor tissues using a Trizol reagent method and quantified using a PCR machine. Primers listed in Table 1 were used as primers.

TABLE 1

| Target Gene | SEQ ID NO: | Primer Sequence Listing |
|---|---|---|
| mBcl2 | SEQ ID NO: 1 | F: 5'- ACT TCG CAG AGA TGT CCA GTC A -3' |
|  | SEQ ID NO: 2 | R: 5'- TGG CAA AGC GTC CCC CTC -3' |
| mFoxp3 | SEQ ID NO: 3 | F: 5'- GGC CCT TCT CCA GGA CAG A -3' |
|  | SEQ ID NO: 4 | R: 5'- GCT GAT CAT GGC TGG GTT GT -3' |

TABLE 1-continued

| Target Gene | SEQ ID NO: | Primer Sequence Listing |
|---|---|---|
| mIL-10 | SEQ ID NO: 5 | F: 5'- CCC TTT GCT ATG GTG TCC TT -3' |
|  | SEQ ID NO: 6 | R: 5'- TGG TTT CTC TTC CCA AGA CC -3' |
| mPerforin1 | SEQ ID NO: 7 | F: 5'- CTG GCT CCC ACT CCA AGG TA -3' |
|  | SEQ ID NO: 8 | R: 5'- GGC TGT AAG HAC CGA GAT GC -3' |
| m β-actin | SEQ ID NO: 9 | F: 5'- ATG CCA CAG GAT TCC ATA CC -3' |
|  | SEQ ID NO: 10 | R: 5'- GAC GGC CAG GTC ATC ACT AT -3' |

Reference Example 6

For ex vivo cytotoxicity assay, tumor cells in mouse spleens were stimulated with 100 μg/ml MC38 cell lysate and 50 ng/ml IL-2 for five days. Thereafter, effector cells and MC38 cells were co-cultured at effector to target (E:T) ratios of 10:1 and 20:1 for four hours. In addition, the cytotoxic capability of immune cells against the tumor cells was tested. For in vitro assay, the mice stabilizing macrophages (J774A.1) and dendritic cells (DC2.4) stimulated with 1 MOI and 10 MOIs of *Mycobacterium paragordonae* thermally sterilized for 24 hours and 48 hours were used as effector cells. In addition, in order to determine whether the cytotoxic capability is exhibited against various cancer cell lines, macrophages were stimulated with 1 MOI, 5 MOI and 10 MOI of the thermally stabilized *Mycobacterium paragordonae* for 24 hours, and then co-cultured with human derived lung cancer cell line (A549), liver cancer cell line (HepG2), and murine bladder cancer cell line (Mbt-2) for four hours. Then, levels of lactate dehydrogenase (LDH) were measured on the culture supernatant using a Cyto-Tox96 non-radioactive cytotoxicity assay kit (Promega, USA).

Reference Example 7. Natural Killer (NK) Cell Activity Assay

The activities of NK cells in the spleen were evaluated using YAC-1 cells. In detail, YAC-1 cells were labeled with CFSE (Thermo) and co-cultured with effector cells at an ET ratio of 20:1 for four hours. The culture supernatant was used for measurement of LDH, and the cells were assayed with FACS to investigate CFSE intensities.

Reference Example 8. Cytokine and Humoral Immune Antibody Assay

To evaluate cytokines generated from the effector cells, TNF-α, IFN-β, IFN-γ, IL-2, IL-10 and IL-12 were measured with culture supernatant using an ELISA kit (eBioscience) according to manufacturer's instructions. In addition, for comparison of humoral immune responses, IgG1, IgG2a and total IgG (eBioscinece) were measured in mouse serum samples of a test group. The concentrations of cytokines and antibodies were assayed by measuring absorbance using a Tecan Microplate Reader (Infinite® M1000 PRO, Switzerland).

Reference Example 9. Flow Cytometry

Spleen cells of mice or immune cells in tumor tissues were assayed using a flow cytometer. In detail, the isolated tumor cells and spleen cells were all stained with CD3-BC421 (1:100, BD Pharmingen), CD4-PE-Cy5 (1:100, BD Pharmingen), CD8-APC-Cy7 (1:100, eBioscience), and NK1.1-PE (1:100, BD Pharmingen), followed by fixing the cells, and antibodies were permeabilized into the cells using a fixation/permeabilization kit (eBioscience) according to manufacturers instructions. TNF-α in the fixed cells was stained with antibody-TNF-α-FITC (1:100, BD Pharmingen). The thus prepared cells were assayed using BD LSR-Fortessa™ X-20 flow cytometer.

Reference Example 10. Statistical Analysis

For comparison of statistical significances, Student's t-test was performed. Data were all represented by mean±standard deviation (SD), and assayed using graph pad software (Prism 5, version 5.01). The statistical significance was denoted by an asterisk as follows: *p=0.05; p≤0.01, *p≤0.001.

Example 1. Preparation of Thermally Inactivated *Mycobacterium paragordonae*

Thermally inactivated, dead *Mycobacterium paragordonae* (KCTC 12628BP) was prepared in the following manner, and *Mycobacterium bovis* BCG was prepared as a control group.

First, *Mycobacterium paragordonae* was inoculated to a 7H9 liquid culture medium containing 10% albumin dextrose catalase (ADC), 2.4% glycerol and 0.2% polysorbate 80. Thereafter, *Mycobacterium paragordonae* was cultured at 30° C., and *Mycobacterium bovis* BCG was cultured at 37° C. until the stationary phase. The strains under the stationary phase were resuspended with a 1% polysorbate 80 solution to facilitate absorbance measurement, and then filtered through an insulin syringe to prevent granulation. Then, based on the colony-forming unit (CFU) depending on the identified absorbance, the dose of the strains was adjusted to $1 \times 10^8$ CFU ($OD_{600}$ 1.0=$1 \times 10^8$ CFU/ml), and then sterilized using a high-pressure steam sterilizer under 121° C. and 1.5 atm conditions for 15 minutes. A solution loss due to high-pressure steam sterilization may adversely affect the concentration of the strains. In this regard, the solution was centrifuged at 13,000 rpm for five minutes to thus obtain *Mycobacterium* pellets, which were then resuspended with a phosphate-based saline (PBS), thereby reducing the error range. The thus prepared thermally inactivated *Mycobacterium* paragordonae and *Mycobacterium bovis* BCG were used in subsequent experiments.

Example 2. Cancer Incidence Delay Effect of *Mycobacterium paragordonae* Injected Prior to Tumor Formation To determine the cancer incidence delay effect of *Mycobacterium paragordonae* administered prior to tumor formation tumor formation, the experiment was carried out according to the dosing regimen shown in FIG. 1A.

In detail, as described in Reference Example 2, the MC38 cell lines were subcutaneously injected to mice, and the thermally inactivated *Mycobacterium paragordonae* prepared in Example 1 was injected into the vicinity of the lymph node of each of the mice at a concentration of $1 \times 10^8/100$ µl after three days following the cell line injection, prior to tumor formation and additionally injected twice at a week interval. Then, the anti-cancer effect was identified. In addition, as described in Reference Example 2, *Mycobacterium bovis* BCG having the same concentration as *Mycobacterium paragordonae* was used as a positive control, and PBS as a solution obtained by suspending the thermally inactivated *Mycobacterium* was used as a negative control. The results are shown in FIGS. 1A to 1E.

FIG. 1A is a diagram showing a dosing regimen of administering *Mycobacterium paragordonae* according to one embodiment to animal models.

FIG. 1B is a graph showing incidence rates of cancer by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

FIG. 1C is a graph showing changes in tumor size by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

FIG. 1D is a graph showing survival rates by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

FIG. 1E shows changes in tumor size by administration of *Mycobacterium paragordonae* according to one embodiment, prior to tumor formation, where Mpg stands for *Mycobacterium paragordonae*; BCG stands for *Mycobacterium bovis* BCG; and PBS is a negative control.

As shown in FIGS. 1A to 1E, the thermally inactivated *Mycobacterium paragordonae* injected prior to tumor formation suppressed tumor incidences by 30% to 50%. However, when the *Mycobacterium bovis* BCG being currently employed for immunotherapy was administered, tumors were formed to all mice. In addition, the thermally inactivated *Mycobacterium paragordonae* delayed not only tumor formation but also cancer incidence, thereby increasing survival rates of the mice by 70% or more. The anti-cancer effect of the *Mycobacterium paragordonae* was confirmed to be statistically significant, compared to the *Mycobacterium bovis* BCG. In addition, when the tumors excised from the mice after completing the experiment were observed with the naked eye, it was confirmed that the tumor sizes were noticeably reduced by administering the thermally inactivated *Mycobacterium paragordonae*.

These results suggest that the *Mycobacterium paragordonae* can be useful as an effective therapeutic agent substituting for the *Mycobacterium bovis* BCG currently being used after surgical operation. It was also confirmed that there was a likelihood of lowering the recurrence of tumors when the *Mycobacterium paragordonae* was injected to tissues surrounding potentially cancerous tumor cells after tumor excision.

Example 3. Anti-Cancer Effect of *Mycobacterium paragordonae* Injected After Tumor Formation To determine the anti-cancer effect of *Mycobacterium paragordonae* after tumor formation, the experiment was carried out according to the dosing regimen shown in FIG. 2A.

In detail, the MC38 cell lines were subcutaneously injected to mice, as described in Reference Example 2, and one week later, it was confirmed that tumors were formed in all mice. Then, the anti-cancer effect of the *Mycobacterium paragordonae* was identified in the same manner as in Example 2. The results are shown in FIGS. 2A to 2E.

FIG. 2A is a diagram showing a dosing regimen of administering *Mycobacterium paragordonae* according to one embodiment to animal models.

FIG. 2B is a graph showing changes in tumor size following tumor formation, by administration of *Mycobacterium paragordonae* according to one embodiment, where Mpg stands for *Mycobacterium paragordonae*; BCG stands for *Mycobacterium bovis* BCG; and PBS is a negative control.

FIG. 2C is a graph showing survival rates following tumor formation, by administration of *Mycobacterium paragordonae* according to one embodiment, where Mpg stands for *Mycobacterium paragordonae*; BCG stands for *Mycobacterium bovis* BCG; and PBS is a negative control.

FIG. 2D shows changes in tumor size following tumor formation, by administration of *Mycobacterium paragordonae* according to one embodiment, where Mpg stands for *Mycobacterium paragordonae*; BCG stands for *Mycobacterium bovis* BCG; and PBS is a negative control.

FIG. 2E shows tumor weights measured at 24 days following tumor formation, by administration of *Mycobacterium paragordonae* according to one embodiment, where Mpg stands for *Mycobacterium paragordonae*; BCG stands for *Mycobacterium bovis* BCG; and PBS is a negative control.

As shown in FIGS. 2A to 2E, the thermally inactivated *Mycobacterium paragordonae* delayed tumor growth speeds, leading to increases in the survival rates of mice by 70% or more. Such an anti-cancer effect was found to be more statistically significant than that of the *Mycobacterium bovis* BCG as a positive control. In addition, when the tumors excised from the mice after completing the experiment were compared with those of the negative or positive control, reduction in the tumor size by administration of the thermally inactivated *Mycobacterium paragordonae*, was observed with the naked eye. Additionally, it was confirmed that the tumor weight was significantly reduced by treatment with the thermally inactivated *Mycobacterium paragordonae* than with the negative or positive control.

These results suggest that the *Mycobacterium paragordonae* can be useful not only as an effective therapeutic agent for treating a cancer disease being in progress but also as a substitute for the existing *Mycobacterium bovis* BCG used as a therapeutic agent only for an early-stage bladder cancer.

Example 4. Assay for Anti-Cancer Vaccine Activity of *Mycobacterium paragordonae*

It was identified whether apoptosis of tumor cells was induced by *Mycobacterium paragordonae*.

In detail, a TUNEL assay was carried out, as described in Reference Example 3, and the results thereof are shown in FIGS. 3A and 3B. In addition, the expression levels of Bcl-2 and Perforin were assayed, as described in Reference Example 4, and the results thereof are shown in FIGS. 3C and 3D. In addition, immunohistochemistry (IHC) assays were performed on perforin and granzyme, as described in Reference Example 4, and the result thereof is shown in FIG. 3E.

FIG. 3A shows the results of tumor cell apoptosis (the left panel), by administration of *Mycobacterium paragordonae* according to one embodiment, as determined by TUNEL assay, where Mpg stands for *Mycobacterium paragordonae*; BCG stands for *Mycobacterium bovis* BCG; and PBS is a negative control.

FIG. 3B is a graph showing the quantification results of apoptotic tumor cells, by administration of *Mycobacterium paragordonae* according to one embodiment, as determined by TUNEL assay, where Mpg stands for *Mycobacterium paragordonae*; BCG stands for *Mycobacterium bovis* BCG; and PBS is a negative control.

FIG. 3C is a graph showing the inhibited expression of Bcl-2 by administration of *Mycobacterium paragordonae* according to one embodiment, where Mpg stands for *Mycobacterium paragordonae*; BCG stands for *Mycobacterium bovis* BCG; and PBS is a negative control.

FIG. 3D is a graph showing the increased expression of perforin by administration of *Mycobacterium paragordonae* according to one embodiment, where Mpg stands for *Mycobacterium paragordonae*; BCG stands for *Mycobacterium bovis* BCG; and PBS is a negative control.

FIG. 3E shows the expression levels of perforin and granzyme by administration of *Mycobacterium paragordonae* according to one embodiment, as determined by IHC assay, where Mpg stands for *Mycobacterium paragordonae*; BCG stands for *Mycobacterium bovis* BCG; and PBS is a negative control.

As shown in FIGS. 3A to 3E, it was confirmed that the apoptosis level of tumor cells was higher in treatment with the *Mycobacterium paragordonae* than with the thermally inactivated *Mycobacterium bovis* BCG as a positive control. In addition, when fluorescence images of apoptotic tumor cells were digitized for comparison, it was confirmed that apoptosis level in the treatment with the thermally inactivated *Mycobacterium paragordonae* was statistically significant and noticeably high. When the expression levels of a gene Bcl-2 inhibiting apoptosis and perforin and granzyme as cytotoxic proteins were comparatively assayed, it was confirmed that the administration of the thermally inactivated *Mycobacterium paragordonae* decreased the expression level of Bcl-2, or increased the expression levels of perforin and granzyme.

Since the tumor cell apoptosis inhibits the growth of tumor cells, cancer development can be prevented while minimizing cancer metastasis to other visceral organs. Despite the importance of the apoptosis for cancer treatment, no apoptosis was detected in the treatment with the *Mycobacterium bovis* currently being commercialized. However, the *Mycobacterium paragordonae* treatment confirmed that the *Mycobacterium paragordonae* had the activity of significantly inducing the apoptosis of tumor cells. Therefore, the *Mycobacterium paragordonae* can be advantageously used in inhibiting cancer development and metastasis while ameliorating the prognosis of disease.

Example 5. Assay for Increased Inflammation Inducing Activity of *Mycobacterium paragordonae* Under Tumor Environments The increased inflammation inducing activity of *Mycobacterium paragordonae* under tumor environments was assayed.

In detail, as described in Reference Example 4, H&E staining was performed, and the result thereof is shown in FIG. 4A. In addition, as described in Reference Example 5, the expression levels of IL-10 and FoxP3 were assayed, and the result thereof is shown in FIG. 4B. In addition, as described in Reference Example 4, IHC assay was performed on CD8 T cells, and the result thereof is shown in FIG. 4C. Additionally, the CD4 and CD8 T cells which secrete TNF-α that induces cytotoxicity and natural killer cells are shown in FIG. 4D.

FIG. 4A shows the results of tumor cell apoptosis, by administration of *Mycobacterium paragordonae* according to one embodiment, as determined by H&E staining, where Mpg stands for *Mycobacterium paragordonae*; BCG stands for *Mycobacterium bovis* BCG; and PBS is a negative control.

FIG. 4B is a graph showing the expression levels of IL-10 and FoxP3 by administration of *Mycobacterium paragordonae* according to one embodiment, as determined by quantitative real time PCR, where Mpg stands for *Mycobacterium paragordonae*; BCG stands for *Mycobacterium bovis* BCG; and PBS is a negative control.

FIG. 4C shows the number of CD8 T cells in tumor tissues by administration of *Mycobacterium paragordonae* according to one embodiment, as determined by IHC assay, where Mpg stands for *Mycobacterium paragordonae*; BCG stands for *Mycobacterium bovis* BCG; and PBS is a negative control.

FIG. 4D shows proportions of TNF-α releasing CD4 and CD8 T cells and natural killer cells in tumors by administration of *Mycobacterium paragordonae* according to one embodiment, as determined by flow cytometry, where Mpg stands for *Mycobacterium paragordonae*; BCG stands for *Mycobacterium bovis* BCG; and PBS is a negative control.

FIG. 4E is a graph showing the cell mediated toxicity by administration of *Mycobacterium paragordonae* according to one embodiment, where Mpg stands for *Mycobacterium paragordonae*; BCG stands for *Mycobacterium bovis* BCG; and PBS is a negative control.

As shown in FIG. 4A, the cells in tumor tissues of mice injected with PBS as a negative control and the thermally inactivated *Mycobacterium bovis* BCG as a positive control had relatively large and loose nuclei and were identified to have characteristics of tumor cells having multiple nuclei. Conversely, the mice administered with the thermally inactivated *Mycobacterium paragordonae* had relatively small cells in size, and normal cells having condensed nuclei had distinctly defined cellular compartments. These results indicate that immune cells migrated to tumor tissues by the treatment with *Mycobacterium paragordonae*.

In addition, as shown in FIG. 4B, the transcriptional expression of a gene for synthesizing cytokine IL-10 involving an immune inhibitory response, and FoxP3 as a marker of a regulatory T cell of an immunoregulatory cell, was identified, and the result showed that the thermally inactivated *Mycobacterium paragordonae* enhanced the immune inhibitory response induced by the tumor cells due to migration of the immune cells into tumor tissues.

In addition, as shown in FIG. 4C, the proportions of the cytotoxic T cells (CD8 T cells) for removing tumors were increased by the administration of the thermally inactivated *Mycobacterium paragordonae*, as determined by IHC assay. This does not mean that only the proportion of the cytotoxic T cells was simply increased, and the proportions of the CD4 and CD8 T cells expressing the cytotoxicity-inducing TNF-α and the natural killer cells were all increased, as determined by flow cytometry, as shown in FIG. 4D.

These results suggest that the *Mycobacterium paragordonae* according to one embodiment is capable of increasing immune cells for removing tumors by more effectively inhibiting immunity reduction in the cancer microenvironment while the *Mycobacterium bovis* BCG as a positive control inhibits the expression of two genes associated with immunity reduction.

Example 6. Assay for Natural Killer Cell or T Cell Mediated Cytotoxic Activity of *Mycobacterium paragordonae*

The cytotoxicity response capable of removing cancer cells is typically mediated by a natural killer cell and a cytotoxic T lymphocyte (CTL). Hence, following the Example 5, it was determined whether the stimulation with the thermally inactivated *Mycobacterium paragordonae* induced the augmented apoptosis of tumor cells by T cell or NK cell mediation.

In detail, as described in Reference Example 6, the cell mediated cytotoxicity was assayed, and the result thereof is shown in FIG. 4E. In addition, as described in Reference Example 7, the natural killer cell activity was assayed, and the results thereof are shown in FIGS. 4F and 4G.

FIG. 4E is a graph showing the cell mediated toxicity by administration of *Mycobacterium paragordonae* according to one embodiment, where Mpg stands for *Mycobacterium paragordonae*; BCG stands for *Mycobacterium bovis* BCG; and PBS is a negative control.

FIG. 4F is a graph showing the cytotoxicity of NK cells by administration of *Mycobacterium paragordonae* according to one embodiment, where Mpg stands for *Mycobacterium paragordonae*; BCG stands for *Mycobacterium bovis* BCG; and PBS is a negative control.

FIG. 4G is a graph showing the cytotoxicity of NK cells by administration of *Mycobacterium paragordonae* according to one embodiment, as determined by flow cytometry, where Mpg stands for *Mycobacterium paragordonae*; BCG stands for *Mycobacterium bovis* BCG; and PBS is a negative control.

As shown in FIG. 4E, the *Mycobacterium bovis* BCG induced increased CTL responses, compared to a negative control, and the *Mycobacterium paragordonae* according to one embodiment induced significantly increased CTL responses, compared to the *Mycobacterium bovis* BCG. These results suggest that the *Mycobacterium paragordonae* has increased capability of inducing antigen-specific CTL responses, compared to the *Mycobacterium bovis* BCG.

In addition, as described in FIG. 4F, an assay for the tumor cell apoptosis mediated by NK cells was performed, and it was confirmed that the *Mycobacterium paragordonae* had significantly increased NK cell mediated cytotoxicity against the YAC-1 cells, compared to the negative or positive control.

In addition, as shown in FIG. 4G, the flow cytometry for CFSE-labeled YAC-1 cells confirmed that the YAC-1 cells demonstrated increased cytotoxicity of about 20%, which is more than twice greater than that of another negative or positive control.

These results suggest that the *Mycobacterium paragordonae* has significantly increased CTL or NK cell mediated cytotoxicity, compared to the *Mycobacterium bovis*, and thus being useful for a cancer immunotherapeutic agent.

Example 7. Assay for Inflammatory Cytokines Secreted from Spleen Cells and Natural Killer Cells Stimulated by *Mycobacterium paragordonae* and Macrophages or Dendritic Cells as Antigen Presenting Cells The macrophages or dendritic cells as antigen presenting cells and the spleen cells and natural killer cells including various immune cells are activated by external stimuli and secrete cytokines such as TNF-α, IFN-γ, IL-2 or IL-12 to induce adaptive immune. In order to restrict immoderate immune responses, a cytokine such as IL-10 is secreted for immune response regulation. Hence, as described in Reference Examples 5 and 6, the expression of TNF-α, IFN-β, IFN-γ, IL-2, IL-10 and IL-12 and the cytotoxic activities were assayed, and the proportions of spleen cells of mice and immune cells in tumors are shown in FIGS. 5A to 5F.

FIG. 5A shows the production of various inflammatory cytokines from spleen cells by stimulation with *Mycobacterium paragordonae* according to one embodiment, where Mpg stands for *Mycobacterium paragordonae*; BCG stands for *Mycobacterium bovis* BCG; and PBS is a negative control.

FIG. 5B shows the production of inflammatory cytokines secreted by stimulating spleen cells with *Mycobacterium paragordonae* according to one embodiment and then restimulating the spleen cells with MC38 tumor cell antigen, where Mpg stands for *Mycobacterium paragordonae*; BCG stands for *Mycobacterium bovis* BCG; and PBS is a negative control.

FIG. 5C shows production of inflammatory cytokines from natural killer cells in spleen cells by stimulation with *Mycobacterium paragordonae* according to one embodiment, where Mpg stands for *Mycobacterium paragordonae*; BCG stands for *Mycobacterium bovis* BCG; and PBS is a negative control.

FIG. 5D is a graph showing the secretion of IL-12 and IL-10 in macrophages (J774A.1) and a dendritic cell (DC.24) by treatment with *Mycobacterium paragordonae* according to one embodiment, where Mpg stands for *Mycobacterium paragordonae*; BCG stands for *Mycobacterium bovis* BCG; and PBS is a negative control.

FIG. 5E shows proportions of IgG1, IgG2a, and total IgG in serums by stimulation with *Mycobacterium paragordonae* according to one embodiment, where Mpg stands for *Mycobacterium paragordonae*; BCG stands for *Mycobacterium bovis* BCG; and PBS is a negative control.

FIG. 5F shows proportions of TNF-α expressing CD8 T cells in the spleen cells to natural killer cells by stimulation with *Mycobacterium paragordonae* according to one embodiment, as determined by flow cytometry, where Mpg stands for *Mycobacterium paragordonae*; BCG stands for *Mycobacterium bovis* BCG; and PBS is a negative control.

As shown in FIGS. 5A to 5C, it was confirmed that a high level of immunity-inducing cytokines such as TNF-α, IFN-γ, IL-2 or IL-12 were secreted from spleen cells stimulated with the thermally inactivated *Mycobacterium paragordonae*, compared to the negative or positive control. Specifically, a high level of TNF-α and IFN-γ were secreted even from natural killer cells in spleen cells.

In addition, as shown in FIG. 5D, a high level of the immunity-inducing cytokine IL-12 was secreted by the stimulation with smaller MOIs of the thermally inactivated *Mycobacterium paragordonae*, which was observed in both macrophages and dendritic cells, compared to the negative or positive control. Conversely, the level of the immunity-suppressing cytokine IL-10 secreted by the stimulation with the thermally inactivated *Mycobacterium paragordonae* was reduced in both macrophages and dendritic cells, compared to the positive control. These results suggest that the immunity was more effectively induced by the *Mycobacterium paragordonae* than by the *Mycobacterium bovis* BCG currently being used for immunotherapy, and thus the anti-cancer effect was enhanced by the induced immune response. In addition, both mouse macrophages and dendritic cells showed increased tumor cytotoxicity by stimulating the thermally inactivated *Mycobacterium paragordonae*, and these effects confirmed that the *Mycobacterium paragordonae* was more effective in terms of tumor cytotoxicity than the *Mycobacterium bovis* BCG currently being commercialized. Additionally, as shown in FIG. 5E, IgG1, IgG2a, and total IgG in serums of mice were measured for humoral immune response comparison, and it was confirmed that the *Mycobacterium bovis* BCG has a significantly increased level of IgG1 for lowering the increased immune responses. Conversely, it was confirmed that the level of IgG2a for inducing a Th1 response by increasing the level of IFN-γ in serums of mice stimulated with the thermally inactivated *Mycobacterium paragordonae* was significantly increased, compared to the positive or negative control.

Therefore, it was identified that the stimulation with the *Mycobacterium paragordonae* induced humoral immunity and secretion of cytokines capable of enhancing immune responses, and activated immune cells for attacking and eliminating tumor cells, thereby maximizing the anti-cancer effect.

Example 8. Assay for Cytotoxic Activity of *Mycobacterium paragordonae* Against Various Cancer Cell Lines Following the Example 7, it was determined whether the stimulation with the thermally inactivated *Mycobacterium paragordonae* induced the augmented apoptosis of tumor cells by the macrophages or dendritic cells.

To determine whether the *Mycobacterium paragordonae* showed cytotoxic capability directly against tumor cells in addition to the inducing of immune cells, cytotoxic activities were assayed at various cancer cell lines.

In detail, a murine colorectal cancer cell line MC38, a human derived, lung cancer cell line A549, a liver cancer cell line HepG2, a lung cancer cell line A549, and a murine bladder cancer cell line Mbt-2, were used as effector cells, and the effector cells were treated with 1, 10, and 20 MOIs of the thermally inactivated *Mycobacterium paragordonae* prepared in Example 1 for 24 hours and 48 hours. Then, cytotoxicity assays were performed, as described in Reference Example 6. The results are shown in FIGS. 6A to 6E.

FIG. 6A is a graph showing the cytotoxicity of a macrophage (J774A.1) for an MC38 colorectal cancer by treatment with *Mycobacterium paragordonae* according to one embodiment, where Mpg stands for *Mycobacterium paragordonae*; BCG stands for *Mycobacterium bovis* BCG; and PBS is a negative control.

FIG. 6B is a graph showing the cytotoxicity of a dendritic cell (DC.24) for an MC38 colorectal cancer cell by treatment with *Mycobacterium paragordonae* according to one embodiment, where Mpg stands for *Mycobacterium paragordonae*; BCG stands for *Mycobacterium bovis* BCG; and PBS is a negative control.

FIG. 6C is a graph showing the cytotoxicity of a macrophages (J774A.1) for an A549 lung cancer cell line by treatment with *Mycobacterium paragordonae* according to one embodiment, where Mpg stands for *Mycobacterium paragordonae*; BCG stands for *Mycobacterium bovis* BCG; and PBS is a negative control.

FIG. 6D is a graph showing the cytotoxicity of a macrophages (J774A.1) for an HepG2 liver cancer cell line by treatment with *Mycobacterium paragordonae* according to one embodiment, where Mpg stands for *Mycobacterium paragordonae*; BCG stands for *Mycobacterium bovis* BCG; and PBS is a negative control.

FIG. 6E is a graph showing the cytotoxicity of a macrophages (J774A.1) for an Mbt-2 bladder cancer cell line by treatment with *Mycobacterium paragordonae* according to one embodiment, where Mpg stands for *Mycobacterium paragordonae*; BCG stands for *Mycobacterium bovis* BCG; and PBS is a negative control.

FIG. 6F is a graph showing the cytotoxicity of the cell culture medium of mouse spleen cells for murine colorectal cancer cell line MC38 by treatment with *Mycobacterium paragordonae* according to one embodiment, where Mpg stands for *Mycobacterium paragordonae*; BCG stands for *Mycobacterium bovis* BCG; and PBS is a negative control.

As shown in FIGS. 6A to 6E, it was confirmed that the cytotoxic capabilities against not only MC38 cell lines in mice but also various cancer cell lines were exhibited by the stimulation with the thermally inactivated *Mycobacterium paragordonae*. This suggests that the anti-cancer effect of the thermally inactivated *Mycobacterium paragordonae* can be demonstrated not only on the MC38 cell lines, that is, the murine colorectal cancer cell lines, but also on the bladder cancer cell line Mbt-2, the human derived liver cancer cell line HepG2 and the lung cancer cell line A549, and thus being applied to various cancer cell lines. Additionally, as shown in FIG. 6F, the cytotoxicity against the MC38 cell was demonstrated on the culture medium containing spleen cells stimulated with the thermally inactivated *Mycobacterium paragordonae*, confirming that the materials contained in the culture medium demonstrated the anti-cancer effect.

Example 9. Combination Therapy Using *Mycobacterium paragordonae* with Anti-Cancer Agent To maximize the anti-cancer effect of *Mycobacterium paragordonae*, the experiment for a combination therapy was carried out on the *Mycobacterium paragordonae* used in combination with an anti-cancer agent, as shown in FIG. 7A.

In detail, as described in Reference Example 2, MC38 cell lines were subcutaneously injected into mice for tumor formation. Then, as described in Reference Example 2, $1 \times 10^8/100$ μl of the thermally inactivated *Mycobacterium paragordonae* prepared in Example 1 was subcutaneously injected into the vicinity of the lymph node of each mouse, and additionally injected three times at an interval of three days for observing the anti-cancer effect. In order to confirm the combination administration effect, Cisplatin (50 μg/kg) was intraperitoneally administered three times at a week interval in combination with the administration of the thermally inactivated *Mycobacterium*.

Thereafter, the tumor sizes and survival rates were determined in the same manner as in Example 2, and the results thereof are shown in FIGS. 7A to 7C.

FIG. 7A is a diagram showing a dosing regimen of administering *Mycobacterium paragordonae* according to one embodiment to animal models to identify the effect of combination administration.

FIG. 7B is a graph showing changes in tumor size by administration of *Mycobacterium paragordonae* according to one embodiment, to identify the effect of combination administration, where Mpg stands for *Mycobacterium paragordonae*; Cis+Mpg stands for Cisplatin and *Mycobacterium paragordonae*; Cisplatin stands for Cisplatin administered alone; and PBS is a negative control.

FIG. 7C is a graph showing survival rates by administration of *Mycobacterium paragordonae* according to one embodiment, to identify the effect of combination administration, where Mpg stands for *Mycobacterium paragordonae*; Cis+Mpg stands for administration of Cisplatin and *Mycobacterium paragordonae* administered in combination; Cisplatin stands for Cisplatin administered alone; and PBS is a negative control.

As shown in FIGS. 7A to 7C, it was confirmed that the anti-cancer effect was synergistically enhanced by the combination administration of the *Mycobacterium paragordonae* in combination with an anti-cancer agent, compared to the single administration of the anti-cancer agent.

The *Mycobacterium paragordonae* used in the present application can be advantageously used for treatment of various types of cancers owing to its capability of inducing an immune response. Considering that the anti-cancer effect can be maximized in a combination administration mode, like in this embodiment, the *Mycobacterium paragordonae* proposed in the present application is expected to be useful as an effective therapeutic agent for various types of cancers in combination with particular anti-cancer agents specific to particular cancers.

While example embodiments of the present application have been described in detail, the scope of the present application is not defined thereby, but various modifications and improvements made by one skilled in the art using basic concepts of the present application defined by the claims are to be construed as being also included in the present application.

Unless otherwise defined, all terms (including technical and scientific terms) used herein have the same meaning as commonly understood by one of ordinary skill in the art to which this disclosure belongs. The contents of all publications described in the present invention as reference documents are introduced to the present invention.

The invention claimed is:

1. A method for treating a solid cancer, the method comprising administering to a subject suffering from solid cancer a therapeutically effective amount of *Mycobacterium paragordonae*.

2. The method of claim 1, wherein the *Mycobacterium paragordonae* is a dead bacterium.

3. The method of claim 2, wherein the dead bacterium is a dead *Mycobacterium paragordonae* resulting from heat treatment.

4. The method of claim 1, wherein the *Mycobacterium paragordonae* is a strain of Deposition No. KCTC 12628BP.

5. The method of claim 1, wherein the cancer is one selected from the group consisting of lung cancer, pancreatic cancer, stomach cancer, liver cancer, colorectal cancer, brain cancer, breast cancer, thyroid cancer, bladder cancer, esophageal cancer, leukemia, ovarian cancer, melanoma, head and neck cancer, skin cancer, prostate cancer, rectal cancer, hepatocellular cancer, and cervical cancer.

6. The method of claim 1, wherein the *Mycobacterium paragordonae* is administered in combination with an anti-cancer agent.

7. The method of claim 1, wherein the *Mycobacterium paragordonae* suppresses the expression or activity of interleukin (IL)-10, or increases the expression or activity of TNF-α, IFN-γ, IL-2, or IL-12.

8. The method of claim 1, wherein the *Mycobacterium paragordonae* increases the cancer cytotoxicity of macrophages or dendritic cells or induces a humoral immune response.

9. The method of claim 1, wherein the number of *Mycobacterium paragordonae* administered to the subject comprises $10^3$ to $10^{11}$ *Mycobacterium paragordonae*.

10. The method of claim 1, wherein the dose of *Mycobacterium paragordonae* administered to the subject comprises $1 \times 10^3$ to $1 \times 10^{11}$ cfu/ml.

11. The method of claim 1, wherein the *Mycobacterium paragordonae* is a live bacterium.

* * * * *